(12) United States Patent
Ribi

(10) Patent No.: US 9,217,736 B2
(45) Date of Patent: *Dec. 22, 2015

(54) TUNABLE DIRECTIONAL COLOR TRANSITION COMPOSITIONS AND METHODS OF MAKING AND USING THE SAME

(71) Applicant: Segan Industries, Inc., Burlingame, CA (US)

(72) Inventor: Hans O. Ribi, Hillsborough, CA (US)

(73) Assignee: Segan Industries, Inc., Burlingame, CA (US)

( * ) Notice: Subject to any disclaimer, the term of this patent is extended or adjusted under 35 U.S.C. 154(b) by 104 days.

This patent is subject to a terminal disclaimer.

(21) Appl. No.: 14/040,461

(22) Filed: Sep. 27, 2013

(65) Prior Publication Data

US 2014/0106963 A1 Apr. 17, 2014

Related U.S. Application Data

(63) Continuation of application No. 12/643,887, filed on Dec. 21, 2009, now Pat. No. 8,569,208.

(60) Provisional application No. 61/238,584, filed on Aug. 31, 2009, provisional application No. 61/140,563, filed on Dec. 23, 2008.

(51) Int. Cl.
*B41M 5/30* (2006.01)
*B41M 5/333* (2006.01)
*G01N 31/22* (2006.01)
*C09D 11/50* (2014.01)
*B41M 5/28* (2006.01)
*B41M 5/323* (2006.01)

(52) U.S. Cl.
CPC ........... *G01N 31/229* (2013.01); *B41M 5/3331* (2013.01); *B41M 5/3333* (2013.01); *C09D 11/50* (2013.01); *G01N 31/222* (2013.01); *B41M 5/282* (2013.01); *B41M 5/287* (2013.01); *B41M 5/305* (2013.01); *B41M 5/323* (2013.01); *B41M 2205/04* (2013.01)

(58) Field of Classification Search
CPC .... B41M 5/3333; B41M 5/30; B41M 5/3055; B41M 5/323; B41M 5/333; B41M 5/3331; B41M 2205/04; G01N 31/22; G01N 31/222; G01N 31/229; C09D 11/50
USPC ...................... 503/200–226; 106/31.14–31.24
See application file for complete search history.

(56) References Cited

U.S. PATENT DOCUMENTS

| | | | |
|---|---|---|---|
| 4,520,376 A | 5/1985 | Morishita et al. |
| 4,717,710 A | 1/1988 | Shimizu et al. |
| 5,085,801 A | 2/1992 | Thierry et al. |
| 5,250,492 A | 10/1993 | Dotson et al. |
| 5,514,635 A | 5/1996 | Filo |
| 5,817,599 A | 10/1998 | Iida et al. |
| 6,022,648 A | 2/2000 | Jacobson et al. |
| 6,046,455 A | 4/2000 | Ribi et al. |
| 6,103,459 A | 8/2000 | Diel |
| 6,241,913 B1 | 6/2001 | Angelopoulos et al. |
| 6,465,791 B1 | 10/2002 | Ribi et al. |
| 6,544,925 B1 | 4/2003 | Prusik et al. |
| 6,579,826 B2 | 6/2003 | Furuya et al. |
| 6,607,744 B1 | 8/2003 | Ribi |
| 6,866,863 B2 | 3/2005 | Ribi |
| 2003/0143188 A1 | 7/2003 | Ribi |
| 2005/0109984 A1 | 5/2005 | Potyrailo et al. |
| 2007/0251912 A1 | 11/2007 | Sixou et al. |

FOREIGN PATENT DOCUMENTS

| | | |
|---|---|---|
| WO | 9939167 | 8/1999 |
| WO | 0200920 | 1/2002 |
| WO | 03037391 | 5/2003 |
| WO | 2004090629 | 3/2004 |
| WO | 2005028524 | 3/2005 |
| WO | 2005029163 | 3/2005 |
| WO | 2005036109 | 4/2005 |
| WO | 2005123023 | 12/2005 |
| WO | 2007111702 | 10/2007 |
| WO | 2008051550 | 5/2008 |
| WO | 2008079357 | 7/2008 |

*Primary Examiner* — Bruce H Hess

(74) *Attorney, Agent, or Firm* — Bret E. Field; Khin K. Chin; Bozicevic, Field & Francis LLP

(57) ABSTRACT

Color change compositions that transition from a first to second color state upon application of an applied stimulus are provided. Also provided are substrates having the compositions on a surface thereof, as well as methods of making and using the compositions.

21 Claims, No Drawings

TUNABLE DIRECTIONAL COLOR TRANSITION COMPOSITIONS AND METHODS OF MAKING AND USING THE SAME

CROSS-REFERENCE TO RELATED APPLICATIONS

Pursuant to 35 U.S.C. §119 (e), this application claims priority to the filing date of U.S. Provisional Patent Application Ser. No. 61/238,584 filed Aug. 31, 2009 and U.S. Provisional Patent Application Ser. No. 61/140,563 filed Dec. 23, 2008; the disclosures of which applications are herein incorporated by reference.

SUMMARY

The invention involves tunable phase controllable systems for generating color development reversibly, irreversibly, form colorless to a colored state based on ascending temperature, from a colored state to a colorless state based on descending temperature, solvation, hydration, or other chemical and physical stimuli to a colored state to a colorless state during the stimuli. Color transitions can be with and without color change hysteresis, including abrupt or broad transition color change options, utilize micro-encapsulation processes or un-encapsulated processes, and can find use in a wide range of applications. Natural product food-grade color developers are described for both ascending and descending color change compositions. Further enabled are combinatorial chemistries including leuco dye color formers and polydiacetylenic-based compounds that serve both as developers and possess their own intrinsic color change properties are described herein.

DETAILED DESCRIPTION

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Compositions of the invention find use in a variety of applications, including but not limited to early stage production, manufacturing, or synthesis stages through to end-of-use indication where a product or good being monitored using an indicator or composition has already expired and is no longer of any further utility or value.

The invention discloses tunable phase controllable systems for generating color development reversibly, irreversibly, from colorless to a colored state based on ascending temperature, from a colored state to a colorless state based on descending temperature, solvation, hydration, or other chemical and physical stimuli to a colored state to a colorless state during the stimuli. Color transitions can be with and without color change hysteresis, including abrupt or broad transition color change options, utilize micro-encapsulation processes or un-encapsulated processes, and can find use in a wide range of applications. Natural product food-grade color developers are described for both ascending and descending color change compositions. Further enabled are combinatorial chemistries including leuco dye color formers and polydiacetylenic-based compounds that serve both as developers and possess their own intrinsic color change properties which may or may not be utilized in conjunction with the invention and are described herein.

Tunable temperature indicating compositions can find use for a wide range of temperature, sensing, indicating, measurement, marking, cold-chain-management, perishable composition monitoring, safety, sensitizing, industrial, food service, pharmaceutical, industrial, processing, food processing, consumer products, household products, toy products, publishing, advertising, promotional dental, security, pharmaceutical, food products, novel packaging, skin care and skin health, pressure monitoring, temperature monitoring, humidity monitoring, time monitoring, environmental monitoring, inventory monitoring, medical and other market and/or product applications and the like.

Example Permutations of Tunable Color Change Options:

Example permutations of tunable color change options include, but are not limited to: reversible color to colorless based on temperature, reversible colorless to color based on temperature, reversible color to colorless based on hydration, reversible colorless to color based on hydration, reversible color to colorless based on solvation, reversible colorless to color based on salvation, irreversible colorless to color based on temperature, irreversible color to colorless based on solvation, reversible non-hysteresis color change, reversible color change with hysteresis types, irreversible non-hysteresis color change, irreversible color change with hysteresis types, hard/abrupt transition types using precise melting point compositions as solvents, a wide range of temperature transition types and ranges, single color change transition types, multiple color change transition types, and the like.

Reversible color development systems rather than conventional color extinction systems have been of interest. Herein we provide simple systems for developing color at increasing temperatures where the color development process can be reversed during descending temperatures.

Simple addition of phase separation compounds that act as developers in the fluid or liquid state can interact with corresponding color developers to develop a color during an elevated temperature phase. During the cooling phase, the color developer phase separates and its ability to interact as a color developer is diminished or eliminated such that the cooling process gives rise to a loss of color. Conversely, as the temperature is elevated again and a phases separated color developer becomes molten, mobile and capable of interacting with the color developer, a color is generated. Importantly, the process is reversible. Of further importance, the process, temperature settings, color types, hysteresis, and complexity of color change can be tuned by varying degrees depending upon the composition of matter in the color development system.

Systems described herein can be non-microencapsulated or micro-encapsulated depending on the formulation and product application of interest. A wide range of micro-encapsulation processes can be utilized in conjunction with the invention described.

Aspects of the embodiments of the invention include a color former and color developer. A variety of different types of color formers may be employed, where examples of different color formers (e.g., dyes) are listed below and specific examples are reported in the experimental section below.

Combined color former, e.g., leuco dye, systems can now allow for new previously unobtainable color changes such as red to green or green to red whereby two leuco dyes mixed together include a color to colorless dye and a colorless to colored dye system. The resulting combination of color to colorless and colorless to color in different combinations permits the possibility of heretofore not realized color overlap such that stationary colors do not interfere with the initial or final color.

Co-Developer/Solvent Systems for Reversible Ascending Temperature Dependent Color Development:

Co-developer/solvent color developer co-monomer including, but not limited to glycerol monostearate derivatives, low acidic phase associating compounds, mild protonating phase associating compounds, and the like. Importantly, single component systems that provide the benefit of being both a solvent for promoting temperature dependent phase change as well as a color developer that works in conjunction with a color former has an advantage of facilitating developing color upon increasing temperature.

Importantly, co-developer/solvent compounds can assist in controlling the ability of a developer by its ability to anneal or un-anneal depending on phase transition to create or abandon a charge transfer complex through phase dissociation and association processes. Importantly, often co-developer/solvent compounds will be esterified with hydroxyl containing groups. Derivatives include, but are no limited to:

2,3-dihydroxypropyl C5
2,3-dihydroxypropyl C7
2,3-dihydroxypropyl C8
2,3-dihydroxypropyl C9
2,3-dihydroxypropyl C10
2,3-dihydroxypropyl C11
2,3-dihydroxypropyl C12
2,3-dihydroxypropyl C13
2,3-dihydroxypropyl C14
2,3-dihydroxypropyl C15
2,3-dihydroxypropyl C16
2,3-dihydroxypropyl C17
2,3-dihydroxypropyl C18
2,3-dihydroxypropyl C19
2,3-dihydroxypropyl C20
2,3-dihydroxypropyl C21
2,3-dihydroxypropyl C22
2,3-dihydroxypropyl C23
2,3-dihydroxypropyl C24
2,3-dihydroxypropyl C25
2,3-dihydroxypropyl C26
2,3-dihydroxypropyl C27
2,3-dihydroxypropyl C28
2,3-dihydroxypropyl C29
2,3-dihydroxypropyl C30
3,4-dihydroxybutyl C5
3,4-dihydroxybutyl C6
3,4-dihydroxybutyl C7
3,4-dihydroxybutyl C8
3,4-dihydroxybutyl C9
3,4-dihydroxybutyl C11
3,4-dihydroxybutyl C12
3,4-dihydroxybutyl C13
3,4-dihydroxybutyl C14
3,4-dihydroxybutyl C15
3,4-dihydroxybutyl C16
3,4-dihydroxybutyl C17
3,4-dihydroxybutyl C18
3,4-dihydroxybutyl C19
3,4-dihydroxybutyl C20
3,4-dihydroxybutyl C21
3,4-dihydroxybutyl C22
3,4-dihydroxybutyl C23
3,4-dihydroxybutyl C24
3,4-dihydroxybutyl C25
3,4-dihydroxybutyl C26
3,4-dihydroxybutyl C27
3,4-dihydroxybutyl C28
3,4-dihydroxybutyl C29
3,4-dihydroxybutyl C30

Solvent/developer color developer co-monomer diacetylenic polydiacetylene polymers including, but not limited to derivatives below of, low acidic phase associating compounds, mild protonating phase associating compounds, and the like.

Example Diacetylenic Compounds:
 2,3-dihydroxypropyl-10,12-dodecadiynoate (2,3-DHP-10,12-C12)
2,3-DHP-10,12-C13
2,3-DHP-10,12-C14
2,3-DHP-10,12-C15
2,3-DHP-10,12-C16
2,3-DHP-10,12-C17
2,3-DHP-10,12-C18
2,3-DHP-10,12-C19
2,3-DHP-10,12-C20
2,3-DHP-10,12-C21
2,3-DHP-10,12-C22
2,3-DHP-10,12-C23
2,3-DHP-10,12-C24
2,3-DHP-10,12-C25
2,3-DHP-10,12-C26
2,3-DHP-10,12-C27
2,3-DHP-10,12-C28
2,3-DHP-10,12-C29
2,3-DHP-10,12-C30

Hydrocarbon Based Solvents Including, But Not Limited To:
n-Decane
n-Decene
n-Dodecane
n-Dodecrne
n-Tetradecane
n-Tetradecene
n-Hexadecane
n-Hexadecene
n-Octadecane
n-Octadecene
n-Eicosane
n-Eicosene
Paraffin Blend Ester compounds can include, but are not limited to n-pentadecyl acetate, n-tridecyl butyrate, n-pentadecyl butyrate, n-undecyl caproate, n-tridecyl caproate, n-pentadecyl caproate, n-nonyl caprylate, n-undecyl caprylate, n-tridecyl caprylate, n-pentadecyl caprylate, n-heptyl caprate, n-nonyl caprate, n-undecyl caprate, n-tridecyl caprate, n-pentadecyl caprate, n-pentyl laurate, n-heptyl laurate, n-nonyl laurate, n-undecyl laurate, n-tridecyl laurate, n-pentadecyl laurate, n-pentyl myristate, n-heptyl myristate, n-nonyl myristate, n-undecyl myristate, n-tridecyl myristate, n-pentadecyl myristate, n-pentyl palmitate, n-heptyl palmitate, n-nonyl palmitate, n-undecyl palmitate, n-tridecyl palmitate, n-pentadecyl palmitate, n-nonyl stearate, n-undecyl stearate, n-tridecyl stearate, n-pentadecyl stearate, n-nonyl icosanoate, n-undecyl icosanoate, n-tridecyl icosanoate, n-pentadecyl icosanoate, n-nonyl behenate, n-undecyl behenate, n-tridecyl behenate, and n-pentadecyl behenate. It is desirable for the esterifying group to be hydroxylated in the event that the melting point medium is to be used as a co-developer/solvent in the system.

Co-developer/solvent color developer co-monomers can be added in combination with a color forming agent at various ratios depending on the application, desired color intensity, color development rate, color hue, opacity and the like. Co-developer/solvents can be used from 99.9% total composition weigh to 0.1%. More usually, co-developer/solvents are used from between 99% to 1% by weight. Typically they are used between 90% and 10%. Most often, they will find use from between 80% and 20% by weight total composition.

Of interest are additional solvents that do not block the ascending temperature color development provided by co-developer/solvent compounds yet provide for lowering or raising the temperature transition of a given ascending color change formulation. Additional non-interfering solvents can be mineral oils, low temperature waxes, other branched or non-branched hydrocarbons and the like.

Temperature post adjusting addition solvents can be added at percentages that promote a desired temperature threshold response of interest. They can be added and can be effective from 0.0001% by weight to a soluble monomer composition to greater than 90% by weight. Often, solvent additives will be added from between 0.001% up to 80% by weight. More often modulating additives will be added from between 0.01% up to 70% by weight. Typically, modulating additives will find use from between 0.1% and up to 50% by weight and most often, modulating additives will be useful between 1% and 25% by weight.

Additive Hysteresis Compounds for Ascending and Descending Color Change:

Compositions described herein may further benefit by adding solvent components that can be used to promote temperature hysteresis between the ascending temperature and descending temperature. Compounds of interest include, but are not limited to: stearyl 2-methylbenzoate, cetyl 4-tert-butylbenzoate, behenyl 4-cyclohexylbenzoate, myristyl 4-phenylbenzoate, lauryl 4-octylbenzoate, hexyl 3,5-dimethylbenzoate, stearyl 3-ethylbenzoate, butyl 4-benzylbenzoate, octyl 3-methyl-5-chlorobenzoate, decyl 4-isopropylbenzoate, stearyl 4-benzoyl benzoate, stearyl 1-naphthoate, cetyl phenylacetate, stearyl phenylacetate, phenyl 4-tert-butylbenzoate, 4-chlorobenzyl 2-methyl benzoate, stearyl 4-chlorobenzoate, myristyl 3-bromobenzoate, stearyl 2-chloro-4-bromobenzoate, decyl 3,4-dichlorobenzoate, octyl 2,4-dibromobenzoate, cetyl 3-nitrobenzoate, cyclohexyl 4-aminobenzoate, cyclohexylmethyl 4-amino benzoate, cetyl 4-diethyklaminobenzoate, stearyl 4-aminobenzoate, decyl 4-methoxybenzoate, cetyl 4-methoxybenzoate, stearyl 4-methoxybenzoate, octyl 4-butoxybenzoate, cetyl 4-butoxybenzoate, 4-methoxybenzyl benzoate, cetyl p-chlorophenylacetate, stearyl p-chlorophenylacetate, decyl 3-benzoylpropionate, cyclohexyl 2-benzoyl propionate, myristyl benzoate, cetyl benzoate, stearyl benzoate, 4-chlorobenzyl benzoate, benzyl cinnamate, cyclohexylmethyl cinnamate, benzyl caproate, 4-chlorobenzyl caprate, 4-methoxybenzyl myristate, 4-methoxy benzyl stearate, benzyl palmitate, 4-nitrobenzyl stearate, neopentyl caprylate, neopentyl laurate, neopentyl stearate, neopentyl behenate, cyclohexyl laurate, cyclohexyl myristate, cyclohexyl palmitate, cyclohexylmethyl stearate, 2-cyclohexyl ethyl stearate, stearyl cyclohexylpropionate, 3-phenylpropyl stearate, 4-methoxybenzyl caproate, 4-methoxybenzyl caprate, 2-chlorobenzyl myristate, 4-isopropylbenzyl stearate, phenyl 11-bromolaurate, 4-chlorophenyl 11-bromolaurate, didecyl adipate, dilauryl adipate, dimyristyl adipate, dicetyl adipate, distearyl adipate, dibenzyl sebacate, distearyl tere-phthalate, dineopentyl 4,4'-diphenyldicarboxylate, dibenzyl azodicaroboxylate, trilaurin, trimyristin, tristearin, dimyristin and distearin.

Standard and Non-Standard Micro-Encapsulation Processes:

Microencapsulation may be whereby surrounding or enveloping one substance within another substance on a very small scale, yielding capsules ranging from less than one micron to several hundred microns in size. Microcapsules may be spherically or otherwise shaped, with a defined wall surrounding the core, while others are asymmetrically and variably shaped, with a quantity of smaller droplets of core material embedded throughout the microcapsule. Multiple state types may be microencapsulated (solids, liquids, and gases.

Tunable compositions can be micro-encapsulated or non-micro-encapsulated depending on the application of interest. Encapsulate species provide the inherent robustness for many matrices or mediums such as plastics, certain paints, or robust coatings. Un-micro-encapsulated species provide a lower cost means to utilize said compositions where the compositions can be administered to a product application in fewer least costly steps. Various permutations of encapsulated on un-encapsulated tunable color generation compositions can be utilized. By way of example, but not limitation, developers and color formers can both be un-encapsulated. Alternatively, the developer can be encapsulated where as the color former may be un-encapsulated. In another example, the developer may be un-encapsulated whereas the color former may be encapsulated. In addition, varying degrees of encapsulation may be utilized by one component or another.

Microencapsulation may be achieved by a various standardized and non-standardized techniques depending on the application of interest. Compositions may be microencapsulated with the intention that the core material be confined within capsule walls for a specific period of time. Alternatively, core materials may be encapsulated so that the core material will be released either gradually through the capsule walls, known as controlled release or diffusion, or when external conditions trigger the capsule walls to rupture, melt, or dissolve.

Core materials can include, but are not limited to: the active ingredient or agent, fill, payload, nucleus, or internal phase. The material encapsulating the core is referred to as the coating, membrane, shell, or wall material. Microcapsules may have one wall or multiple shells arranged in strata of varying thicknesses around the core.

Microencapsulated materials are utilized in agriculture, pharmaceuticals, foods, cosmetics and fragrances, textiles, paper, paints, coatings and adhesives, printing applications, safety applications, rapid temperature monitoring, advertising and promotion, low temperature indication, high temperature indication, toy applications, publishing, games, and a wide range other industries and markets.

Carbonless copy paper applications may involve microencapsulated colorless ink that is applied to the top sheet of paper, and a developer is applied to the subsequent sheet. When pressure is applied by writing, the capsules break and the ink reacts with the developer to produce the dark color of the copy.

Others have referred to the use of microencapsulated materials to enhance the properties of finished goods. An increasingly important application utilizes the incorporation of microencapsulated phase change materials. Phase change materials absorb and release heat in response to changes in environmental temperatures. Phase change materials can be purchased from a wide range of chemical vendors (e.g. Microteck Corporation or Bay Materials LLC). With increasing temperatures, the phase change material melts, absorbing excess heat, and feels cool. Conversely, as temperatures fall, the phase change material releases heat as it solidifies, and feels warm. This property of microencapsulated phase change materials can be harnessed to increase the comfort level for users of sports equipment, military gear, bedding, clothing, building materials, and many other consumer products.

Active compositions and agents can be encapsulated to be released over time, allowing farmers to apply the pesticides less often rather than requiring very highly concentrated and perhaps toxic initial applications followed by repeated applications to combat the loss of efficacy due to leaching, evaporation, and degradation. Protecting the active compositions from full exposure to the elements lessens the risk to the environment and those that might be exposed to the chemicals and often provide for a more efficient depoyment.

A wide range of food additives, pharmaceuticals, medications, active compositions, sensitizers, dyes, leuco dyes, diacetylenic monomers, polydiacetylenic materials, polymers in general, pesticides, micro-organisms, flavors, fragrances, stimulants, ingestibles, non-ingestibles, drugs, oxidants, anti-oxidants, and the like can be microencapsulated alone or in combination with the active optical change agents describe herein.

Microencapsulation processes can be categorized by chemical processes and mechanical or physical processes including, but not limited to bulk fluid processes, phase separation processes, chemical processes, mechanical shear processes, milling processes, and commercially available processes. Compositions discussed herein can be microencapsulated using coacervation, interfacial polymerization, polymer-polymer incompatibility, phase separation processes, oil-in-water encapsulation, centrifugal processes, high-shear processes, mechanical drying processes, fluid bed coating, Wusrster processes, centrifugal extrusion, ultrasonication/coating, rotational suspension, double wall micro-encapsulation, chemical silanization processes, liposomal encapsulation, in-line printing/layering processes, heat/chilling cycling, embedding, in-situ polymerization, urea-formaldehyde systems, melaine formaldahyde systems, impregnation, particle coating, and a variety of other micro-particle formation/microencapsulation processes or the like.

Complex coacervation can be employed to provide capsules for use in controlled dry delivery, fragrance samplers, pesticides and cosmetic ingredients. Complex coacervation systems are one of the largest practical applications of products of microencapsulation. In the complex coacervation process gelatin having a high iso-electric point and gum arabic containing many carboxyl groups are added to a core-containing suspension at relatively low pH above 35° C. The gelatin and gum Arabic react to form microdroplets of polymer coacervate which separate. The wall can be susbsequently hardened by several means such as by the addition of formaldehyde or glutaraldehyde. In the final steps, the suspension of microcapsules is cooled and the pH raised after which the suspension is filtered leaving the microcapsules on the filter media. Many variations of complex coacervation are known as well as combinations of polymers. Complex coacervation can employed to encapsulate various tunable compositions describe herein.

Substrate Types Utilized for Coating with Tunable Compositions:

Tunable color change compositions can be applied and utilized with a wide range of substrates (indicating substrates). Indicating substrate compositions include but are not limited to paper, plastic, hard surfaces, soft surfaces, stiff or rigid surfaces, compliant surfaces, printed surfaces, printable surfaces, transparent surfaces, semi-transparent surfaces, opaque surfaces, non-transparent surfaces, skin, finger nails, molded surfaces, flexo-graphic printing surfaces, foam surfaces, expanded plastic surfaces, insulating surfaces, conducting surfaces, conducting ink surfaces, and the like. A substrate composition can be comprised of thick or thin materials ranging in thickness from 1 nanometer to 100 centimeters. Often thicknesses will range from 10 nanometers to 10 centimeters. More often substrates suitable for indicating compositions will range from 1 micron to 1 centimeter. Typical substrates will range from 10 microns to 5 millimeters and most often in the range between 0.1 millimeters and 1.0 millimeters.

Color Formers, Compatible Thermochromic Dye Compounds:

A variety of different color former components may be employed, including thermocrhomic dyes. Thermochromic dyes and colorants of interest can be added to the composition formulation to serve as an indicating means to show that a particular composition has been temperature activated for optimal use. Temperature ranges for thermochromic transitions can be below freezing to above boiling depending on the intended use of the thermchromic composition application. Thermochromic dyes can find use in a variety of compositions and applications and formats. Thermochromic dyes can include but are not limited to compounds including: bis(2-amino-4-oxo-6-methylpyrimidinium)-tetrachlorocuprate (II); bis(2-amino-4-chloro-6-methylpyrimidinium) hexachlorod-icuprate(II); cobalt chloride; 3,5-dinitro salicylic acid; leuco dyes; spiropyrenes, bis(2-amino-4-oxo-6-methylpyrimidinium) tetrachlorocuprate(II) and bis(2-amino-4-chloro-6-methylpyrimidinium) hexachlorodicuprate(II), benzo- and naphthopyrans (Chromenes), poly(xylylviologen dibromide, di-beta-naphthospiropyran, Ferrocene-modified bis(spiropyridopyran), isomers of 1-isopropylidene-2-[1-(2-methyl-5-phenyl-3-thienyl)ethylidene]-succinic anhydride and the Photoproduct 7,7adihydro-4,7,7,7a-tetramethyl-2-phenylbenzo[b] thiophene-5,6-dicarboxylic anhydride, micro-encapsulated dyes, precise melting point compositions, infra-red dyes, spirobenzopyrans, spironnapthooxazines, spirothopyran and related compounds, leuco quinone dyes, natural leuco quinone, traditional leuco quinone, synthetic quinones, thiazine leuco dyes, acylated leuco thiazine dyes, nonacylated leuco thiazine dyes, oxazine leuco dyes, acylated oxazine dyes, nonacylated oxazine leuco dyes, catalytic dyes, combinations with dye developers, arylmethane phthalides, diarylmethane phthalides, monoarylmethane phthalides, monoheterocyclic substituted phthalides, 3-hetercyclic substituted phthalides, diarylmethylazaphthalides, bishetercyclic substituted phthalides, 3,3-bisheterocyclic substituted phthalides, 3-heterocyclic substituted azaphthalides, 3,3-bisheterocyclic substituted azaphthalides, alkenyl substituted phthalides, 3-ethylenyl phthalides, 3,3-bisethylenyl phthalides, 3-butadienyl phthalides, bridged phthalides, spirofluorene phthalides, spirobensanthracene phthalides, bisphthalides, di and triarylmethanes, diphenylmethanes, carbinol bases, pressure sensitive recrcording chemistries, photosensitive recording chemistries, fluoran compounds, reaction of keto acids and phenols, reactions of keto acids with 4-alkoxydiphenylamines, reactions of keto acids sith 3-alkoxdiphenylamines, reactions of 2'-aminofluorans with aralkyl halides, reaction of 3'-chlorofluorans with amines, thermally sensitive recording mediums, tetrazolium salts, tetrazolium salts from formazans, tetrazolium salts from tetazoles, and the like.

Other thermochromic dyes of interest include leucodyes including color to colorless and color to color formulations, vinylphenylmethane-leucocynides and derivatives, fluoran dyes and derivatives, thermochromic pigments, micro and nano-pigments, molybdenum compounds, doped or undoped vanadium dioxide, indolinospirochromenes, melting waxes, encapsulated dyes, liquid crystalline materials, cholesteric liquid crystalline materials, spiropyrans, polybithiophenes, bipyridine materials, microencapsulated, mercury chloride dyes, tin complexes, combination thermochromic/photochromic materials, heat formable materials which change structure based on temperature, natural thermochromic materials such as pigments in beans, various thermochromic inks sold by Securink Corp. (Springfield, Va.), Matusui Corp., Liquid Crystal Research Crop., or any acceptable thermochromic materials with the capacity to report a temperature change or can be photo-stimulated and the like. The chromic change agent selected will depend on a number of factors including cost, material loading, color change desired, levels or color hue change, reversibility or irreversibility, stability, and the like.

Alternative thermochromic materials can be utilized including, but not limited to: light-induced metastable state in a thermochromic copper (II) complex *Chem. Commun.*, 2002, (15), 1578-1579 under goes a color change from red to purple for a thermochromic complex, [Cu(dieten)2](BF4)2 (dieten=N,N-diethylethylenediamine); encapsulated pigmented materials from Omega Engineering Inc.; bis(2-amino-4-oxo-6-methyl-pyrimidinium)-tetrachlorocuprate (II); bis(2-amino-4-chloro-6-methylpyrimidinium) hexachlorod-icuprate(II); cobalt chloride; 3,5-dinitro salicylic acid; leuco dyes; spiropyrenes, bis(2-amino-4-oxo-6-methylpyrimidinium)-tetrachlorocuprate(II); bis(2-amino-4-chloro-6-methylpyrimidinium)hexachlorod-icuprate(II); cobalt chloride; 3,5-dinitro salicylic acid; leuco dyes; spiropyrenes, bis(2-amino-4-oxo-6-methylpyrimidinium)tetrachlorocuprate(II) and bis(2-amino-4-chloro-6-methylpyrimidinium)hexachlorodicuprate(II), benzo- and naphthopyrans (Chromenes), poly(xylylviologen dibromide, di-beta-naphthospiropyran, Ferrocene-modified bis(spiropyridopyran), isomers of 1-isopropylidene-2-[1-(2-methyl-5-phenyl-3-thienyl)ethylidene]-succinic anhydride and the Photoproduct 7,7adihydro-4,7,7,7a-tetramethyl-2-phenylbenzo[b]thiophene-5,6-dicarboxylic anhydride, and the like. Encapsulated leuco dyes are of interest since they can be easily processed in a variety of formats into a plastic or putty matrix. Liquid crystal materials can be conveniently applied as paints or inks to surfaces of color/shape/memory composites.

Thermochromic color to colorless options can include by way of example, but not by limitation: yellow to colorless, orange to color less, red to colorless, pink to colorless, magenta to colorless, purple to colorless, blue to colorless, turquoise to colorless, green to colorless, brown to colorless, black to colorless. Color to color options include but are not limited to: orange to yellow, orange to pink, orange to very light green, orange to peach; red to yellow, red to orange, red to pink, red to light green, red to peach; magenta to yellow, magenta to orange, magenta to pink, magenta to light green, magenta to light blue; purple to red, purple to pink, purple to blue; blue to pink; blue to light green, dark blue to light yellow, dark blue to light green, dark blue to light blue; turquoise to light green, turquoise to light blue, turquoise to light yellow, turquoise to light peach, turquoise to light pink; green to yellow, dark green to orange, dark green to light green, dark green to light pink; brown and black to a variety of assorted colors, and the like. Colors can be deeply enriched using fluorescent and glow-in-the-dark or photo-luminescent pigments as well as related color additives.

Reversible and irreversible versions of the color change agent can be employed depending on the desired embodiment of interest. Reversible agents can be employed where it is desirable to have a multi-use effect or reuse the color change effect. For example, products with continued and repeated use value will find utility of a reversible color change component comprising the final embodiment. In this case it would be desirable to utilize a reversible thermochromic or luminescent material which can be repeated during usage. In another example, it may be desirable to record a single color change permanently. In this case, it would be desirable to utilize a thermochromically irreversible material which changes from one color to another giving rise to a permanent change and indicating that the composition should be discarded after use.

Luminescent or fluorescent pigments can be used in conjunction with co-topo-chemical polymerization compositions. Non-visible spectrum fluorescent dyes can be obscured by an one color of a diacetylenic composition or other thermochromic dye such that when a temperature triggering event occurs, the fluorescent signal becomes visible when utilizing the corresponding wavelength to reveal the fluorescent dye composition.

Natural Food-Grade Descending Color Developers:

Compositions disclosed include carnauba wax as a novel natural single and food grade single component co-developer-solvent that can be for descending color development, Carnauba wax contains mainly esters of fatty acids (80-85%), fatty alcohols (10-16%), acids (3-6%) and hydrocarbons (1-3%). Specific for carnauba wax is the content of esterified fatty diols (about 20%), hydroxylated fatty acids (about 6%) and cinnamic acid (about 10%). Cinnamic acid, an antioxidant, may be hydroxylated or methoxylated.

Good Emulsification Characteristics

Food Grade

Carnauba wax can produce a glossy finish and as such is used in automobile waxes, shoe polishes, food products such as candy corn, instrument polishes, and floor and furniture polishes, especially when mixed with beeswax. It is used as a coating on dental floss. Use for paper coatings is the most common application in the United States. It is the main ingredient in surfboard wax, combined with coconut oil.

Because of its hypoallergenic and emollient properties as well as its shine, carnauba wax appears as an ingredient in many cosmetics formulas where it is used to thicken lipstick, eyeliner, mascara, eye shadow, foundation, deodorant, various skin care preparations, sun care preparations and the like.

Natural co-developer-solvents for descending color development can be used from 99.9% total composition weigh to 1%. More usually, co-developer/solvents are used from between 99% to 1% by weight. Typically they are used between 95% and 5%. Most often, they will find use from between 90% and 20% by weight total composition.

Natural co-developer-solvents provide for low to high temperature range reversible descending temperature color change compositions. By way of example, but not limitation, co-developer-solvents can be formulated using analog compositions of carnauba wax. Longer chain alcohol and or ester compounds can be separated or added during the processing and purification phase of preparing carnauba wax.

Carnauba wax and other related natural formulations can be used to produce reversible color change compositions from below 0° C. to above 150° C. Commonly commercially available leuco dye compositions are typically limited to 70° C. and primarily include synthetic melting point compositions and developers.

Natural Food-Grade Ascending Color Developer:

Compositions disclosed include glycerol monostearate wax as a novel natural and food grade single component co-developer-solvent that can be for descending color development. Glycerol monostearate, popularly known as GMS is an emulsifier compound. GMS is a colorless, odorless and sweet-tasting flaky powder that is hygroscopic. It occurs naturally in the body and in fatty foods. It is formed during the breakdown (metabolism) of fats in the body.

A food additive used as a thickening, emulsifying, anti-sticking, anti-stalant agent; emulsifying agent for oils, waxes and solvents; protective coating for hygroscopic powders; solidifier and control release agent in pharmaceuticals; resin lubricant. Used in cosmetics and hair care products. GMS is largely used in baking preparations to add "body" to the food. It is responsible for giving ice creams and whipped creams its smooth texture.

Natural co-developer-solvents for ascending color development can be used from 99.9% total composition weigh to 1%. More usually, co-developer/solvents are used from between 99% to 1% by weight. Typically they are used between 95% and 5%. Most often, they will find use from between 90% and 20% by weight total composition.

Additional Developers:

A range of alternate developers may be employed for various applications and at different ratios alone or in combination with natural co-solvent-developers described depending on the intended use. Alternate developers included but are not limited to: tert-butylphenol, nonylphenol, dodecyl phenol, styrenated phenols, 2,2-methylene-bis-(4-methyl-6-tert-butylphenol), .alpha.-naphthol, .beta.-naphthol, hydroquinemonomethyl-ether, guaiacol, eugenol, p-chlorophenol, p-bromophenol, o-chlorophenol, o-bromophenol, o-phenyl phenol, p-phenyl phenol, p-(p-chlorophenyl)-phenol, o-(o-chlorophenyl)-phenol, p-methyl hydroxy benzoate, p-ethyl hydroxy benzoate, p-octyl hydroxy benzoate, p-butyl hydroxy benzoate, p-octyl hydroxy benzoate, p-dodecyl hydroxy benzoate, 3-iso-propyl catechol, p-tert-butyl catechol, 4,4-methylene di phenol, 4,4-chio-bis-(6-tert-butyl-3-methyphenol), 1,1-bis-(4-hydroxyphenol)-cyclohexane, 4,4-butylidene-bis-(6-tert-butyl-3-methylphenol, bisphenol A, bisphenol S, 1,2-dioxynaphtaleine, 2,3-dioxynaphthalein, chlorocatechol, bromo catechol, 2,4-dihydroxybenzophenon, pheno phtalein, o-cresol phthalein, methyl protocatechinate, ethyl protocatechinate, propyl protocatechinate, octyl protocatechinate, dodecyl protocatechinate, 2,4,6-trioxymethyl benzene, 2,3,4-trioxyethyl benzene, methyl gallicate, ethyl gallicate, propyl gallicate, butyl gallicate, hexyl gallicate, octyl gallicate, dodecyl gallicate, cetyl gallicate, stearyl gallicate, 2,3,5-trioxynaphthalein, tannin acid and phenol resins.

Additives for Modulating Temperature Transitions:

Various oils including organic, natural, inorganic, and synthetic oils can be added to diacetylenic compositions to up temperature shift or down temperature shift the original diacetylenic composition's intrinsic temperature threshold. Oils can include, but are not limited to corn oil, various vegetables oils, nut oils, root oils, herbal oils, paraffin oils, greases, animal fats, natural extract oils, flavor based oils, aromatic based oils, industrial oils, and the like can be added to assist in modulating the temperature setting of a composition.

Oils based modulating additives or the like can be added at percentages that promote a desired temperature threshold response of interest. Modulating additives can be added and can be effective from 0.0001% by weight to a soluble monomer composition to greater than 90% by weight. Often, modulating additives will be added from between 0.001% up to 80% by weight. More often modulating additives will be added from between 0.01% up to 70% by weight. Typically, modulating additives will find use from between 0.1% and up to 50% by weight and most often, modulating additives will be useful between 1% and 25% by weight.

Additives Including Printing Vehicle Additives for Post Modulating Temperature Transitions:

Constituents may be added to printing vehicles that may be utilized to adjust the initial designated temperature of a formulated thermochromic composition. Resin constituents can include acids, bases, hardening agents, softening agents, hydrating agents, dehydrating agents, effector agents, phase shifting agents or the like.

Temperature post modulating additives or the like can be added at percentages that promote a desired temperature threshold response of interest. Modulating additives can be added and can be effective from 0.0001% by weight to a soluble monomer composition to greater than 90% by weight. Often, modulating additives will be added from between 0.001% up to 80% by weight. More often modulating additives will be added from between 0.01% up to 70% by weight. Typically, modulating additives will find use from between 0.1% and up to 50% by weight and most often, modulating additives will be useful between 1% and 25% by weight.

Optical Pattern and/or Message Development:

Optical patterns can be developed under triggering conditions using optical color change dye systems in combination with modeled substrate surfaces. An image can be generated by applying a pressure indicating film over a substrate layer that has been pre-surface textured or patterned. As temperatures are induced the dye layer initially comes in contact with the close proximity regions or features of the patterned substrate surface. An initial color change will occur in the dye layer the emulates the upper surfaces of the substrate. As temperatures continues to increase, the dye layer may be forced in contact with lower regions of the substrate surface texture. Images or patterns can appear differentially as a result of the final temperature induced between the temperature indicating dye layer and the patterned or textured substrate. Partial images can be made to occur at lower temperatures. More complete or developed images or messages can be made to appear at medium pressures. Fully developed images or completed messages can be made to appear at final desired induced temperature.

Novel Printing Approaches for Discrete Color/Pattern Development:

Inkjet printing, drop-on-demand printing, continuous inkjet printing, multi-color flexographic printing and the like can be utilized to selectively print one or more of a color former, sensitizer, augmenting agent, or color developer composition. Amounts of one or the other component or another can be selectively printed whereby generating image development processes in novel formats.

Transient Reversible Color Development:

Dissolved aqueous formulations of dissolved or ultra-fine aqueous dispersions comprising a color formation compound and a mild color development compound can be produced in situ where by color is immediately developed in the dissolved or dispersed medium. The dissolving and dispersing process may involve solubility mediators such as low or high molecular weight polyethylene glycols. When the pre-colored mixture/medium is applied to or printed on a substrate and dried, the color formation and color development compounds are dissociated so that the color is eliminated. In the dried uncolored state, each component however remains immediately proximal to is interacting pair. Importantly, re-hydration or re-solubilizing the printed surface gives rise to instant color development that will transiently dissipate upon re-drying. The transient reversible color change can be systematically repeated numerous times. The color change can be made permanent by adding fixation agent to the re-hydration or re-solubilizing composition.

Passive and Active RFID Temperature Integrating Devices:

In certain embodiments, energies generated in RFID circuits can be utilized as a stimuli to selectively and locally induce an optical change in color change compositions. Highly sensitive and responsive compositions can be printed selectively and adjoined with a passive or active RFID devices such that radio wave stimuli sent to the RFID device can be utilized to induce a color change dependent response. The response can be triggered in the RFID circuit for the purpose of adding a visual indication means to the RFID device which otherwise, would not only be visible during and RFID tag usage event.

Anti-Oxidants/Preservatives:

Various antidoxidant and/or preservatives may be included in compositions of the invention. Examples of compounds having anti-oxidant and/or preservative activity include, but are not limited to: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Machine-Readable Chemistries and Device Configurations:

In certain embodiments, indicator compositions of the invention find use in machine-readable applications. Machine-readable chemistry and device configurations can include, but are not limited to, various printed barcodes, Interactive barcodes, abuse security barcodes; 1D, 2D, and 3D; barcodes holographic barcodes, vision imaging systems, transient barcodes, time-only barcodes, freshness indicating barcodes, shape memory bar codes, and a variety of other applications and formats.

Compositions herein can be formulated and utilized in a variety of visual, scanning, imaging, and machine readable processes as they relate to temperature monitoring algorithms. Messages or codes can be made to appear or disappear; parts or elements of graphics, symbols or codes can be utilized to make the element, graphic, or code un-discernable or unrecognizable until that portion of the medium has changed with temperature or the like.

Indicator compositions can be utilized in both visual and machine aided formats. Visual readings are made with distinct visual determination of a threshold color change that occurs. Machine aided formats are made using an optical or electrical interpreted change in a color hue or conductive characteristic in a co-topo-polymeric composition that undergoes a state threshold change. By way of example, but not limitation, a composition can be printed or formulated in a machine viewable format. A measurable reading may be taken of an initial colorimetric state. A second or sequential reading can be measured as threshold state occurs. During the transition from one state to another state, an instrumented reading can be registered. The threshold transition can be measured against a calibrated reading such that the degree or magnitude of the state threshold change can be recorded and monitored. Recorded and monitored machine measurements can be displayed by instrumentation utilized in the machine aided format.

Machine readable/responsive barcodes can be utilized for determining the presence of or responding to a temperature fluctuation, visible light, ultra-violet light, irradiation for applications such as food sterilization including gamma and cobalt 60 irradiation levels, hydration, pressure changes, high pressure events including high pressure sterilization, contaminations such a heavy metal contamination, alcohol levels, poisons, chemical sensing, biological compositions, chemical reagents, non-specific analyte binding, specific analyte binding, gases, physical and mechanical responses, UV intensity, light intensity, sanitization conditions, mechanical stress conditions, pressurization formats, oxidation state, optical bleaching, end-of-use indication, time, time and temperature, free radical content, hydration state, skin care health, medical sterilization, clinical health status, indicating sensors on food storage containers medical status, security applications, anti-tampering applications, and any of a number of other measurable indicia.

Machine readable codes for indicating time duration for product shelf-life and use indication can be accomplished using sensing compositions that shift spectrally in response to ambient conditions and product storage.

Also of interest are barcodes embedded or obscured with n indicator composition that is selectively revealed upon triggering at set points of co-topo-polymeric indicator.

A range of barcode languages can be utilized that can be partially of fully associated with a composition and therefore act as a machine readable indication means to measure and report the selective functionality intended to comprise the co-topo-polymeric composition used for indication. Barcode types include, but are not limited to any language, a wide range in size and numbers of character, as well as the barcode language of interest: 39, 93, 128A, 128B, 128C, A standard barcode or UPC code can be obscured, coated, embedded in or over-laid by a mixed or single component chromic change agent. Part of the standard bar code can be clearly visible at the beginning of reading so as to generate an initial starting parameter set. Selective portions of the barcode can be covered by discrete compositions that are set to change color at pre-determined temperature exposures. As the barcode is placed on a product type at a lowered temperature the chromic change agent can be activated. On activation, pre-determined elements of the code will be obscured by the optical density of the chromic change agent (i.e., the indicator composition). The optical density of the barcode will be set such that a barcode reader will not be able register the obscured portion/bars that represent a specific code sequence. As the barcode/product is raised in temperature and as pre-selected temperature are achieved and exposed, a pre-determined section of bar code will be revealed (reversibly or irreversibly depending on the nature of the chromic change agent selected). As each temperature threshold is achieved during the temperature exposure process, each pre-determined/coated barcode region will be come machine readable. In some instances, an indicator may be configured as a linear segmented barcodes that differentially respond to temperature and/or time-temperature along their axis.

Non-readable or partially readable barcodes utilizing single or mixed compositions (e.g., color former compositions) as the obscuring agent are readily scanned for activity or inactivity in part or in whole.

Compositions herein and other blue/black bar codes provide a unique optical masking characteristic that makes a partially readable of fully non-readable part or all of the modified bar code. In addition the transition of a blue/black compositions and compounds to a red or orange hue including but not limited to light pink to dark red hues, provides for high optical readability by most commercial barcode readers since the red, orange, pink or related hues are optically transparent to the red light sources utilized in standard barcode readers.

Readable barcode languages include but are not limited to: Morovia Code 25, 11, 12B. 139. UPC-A, UPC-E, EAN-8, EAN-13, code 128b, USS 39, USD 3, 3 of 9 code, code 39. hibcc. Java applet, logmars, full, symbology, industry 2 of 5, discrete, self checking codes, msi, plesssey, one-dimensional barcodes, two-dimensional barcodes, three-dimensional barcodes, halographic barcodes, luminescent barcodes, and the like.

Barcode formats of interest include, but are not limited to: Off to On switching barcodes; On to off switching barcodes; Codes 39 and 93 for embedded thermal messaging; various barcode geometries, such as planar, curved, round, etc.; barcodes configured for thermal delay for time temperature coding; freshness indicating barcodes; time-only indicating barcode; etc.

In some instances, one may have re-programmable barcodes that can be re-set among, in between or adjacent to a bar code set through re-printing a region of interest.

Time/Low, Medium, and High Temperature Recording Mediums:

Non-aggressive to aggressive adhesives and contact or non-contact compositions can be used in combination with optical development pigmentation as controlled time-dependent activation mechanisms. Commercially available and unique adhesive compositions are disclosed that initiate color development in amenable dried optical pigments. Depending on the aggressive or non-aggressive nature of the pigment, viscosities, additives, promoters, or inhibitors, the color development process can be accelerated to short time durations (hours), to medium time durations (days), longer time durations (weeks), and prolonged time durations (months to years).

A wide range of different printed substrates can be utilized using different printing means such as ink jet printing, drop on demand printing, flexographic printed, rotogravier printing, off-set printing, screen printing or the like. Papers, films, plastics, printed surfaces, metals, composites and a range of other substrates can be utilized.

Applications include, but are not limited to safety products, food, beverage, pharmaceutical, electronics, tickets, promotional, advertising, printing, industrial, commercial, military, procurement, cold chain monitoring, timing indicators for water filters, security badges and applications, security papers, security documentation bags, laser engraving applications, 3-D laser lithography, pharmaceutical perishability monitoring, promotional-time sensitive coupons and product applications, consumer products for various household applications, commercial sanitary products requiring inspection and replacement such add deodorizers and urinal screens, tamper evident applications, self-changing price labels, self-activating lottery tickets, time indication for scholastic testing, inventory timing and control, expiration coupons, full color image development, high temperature/time indication, medium temperature/time indication, low temperature/time indication, product applications as applied to a wide range of consumable and non-consumable products, promotional and advertising applications, food safety and storage products, cooking indicator and sensor designs and manufacturing processes, photochromic, mechanochromic, hydrochromic technologies, pressure indicating technologies, tactochromic technologies, time indicating technologies, temperature threshold monitoring technologies, sensing and reporting technologies, shape/memory plastics, thermal transfer plastics technology, novel material science formulations, thermal expansion compositions, disposable thermometers and devices, various rapid temperature monitoring sensors and compositions, novel technical color change dyes and printing applications, microwave cooking sensors and applications, interactive machine sensor readable formats, ingestibles applications, packaging applications, label applications and constructs, and applications to various industries, product embodiments, and new product categories relating to consumer products, consumer care products including any and all improvements and the like.

Low Temperature Ranges for Time and Time/Temperature Dependent Monitoring:

Low temperature application ranges include ranges in particular for perishable items such as food, beverages, alcoholic beverages, pharmaceutical products, blood, bio-pharmaceutical products, sensitive chemistries, rare materials, biological specimens, virulent bacteria and virus, DNA and RNA storage, and a number of other temperature sensitive items or products that require temperature history and storage conditions to be monitored and recorded. Low temperature applications can range from −200° C. to 25° C.

Medium Temperature Ranges for Time and Time/Temperature Dependent and Monitoring:

Medium temperature applications include ranges further for perishable items that expire at elevated temperatures, warm holding temperatures, monitoring medium temperature processes for process validation and quality control, storage conditions, warming foods, monitoring plant growth conditions, monitoring environmental conditions and living conditions, industrial applications including manufacturing processes, storage of explosives, monitoring shipping storage containers from overseas suppliers, monitoring logistics of foods and goods cross country, in-flight monitoring of air freighted goods, and the like. Medium temperature application can range from 26° C. to 60° C.

High Temperature Ranges for Time and Time/Temperature Dependent Monitoring:

High temperature applications include ranges further for perishable items that expire at elevated temperatures, hot holding temperatures, monitoring hot temperature processes for process validation and quality control, storage conditions, heated foods, monitoring high temperature conditions, hot holding food service applications where time and temperature monitoring is important, monitor food processes that require limited time exposure at elevated temperature for food preparation, re-heating applications, microwave cooking applications where foods need to be heated and maintained at elevated temperatures for complete and thorough cooking, monitoring environmental conditions and living conditions, industrial applications including manufacturing processes, storage of military items, high temperature monitoring shipping storage containers from overseas suppliers, novel autoclave and sterilization conditions, medical equipment sterilization, monitoring logistics of foods and goods cross country, in-flight monitoring of air freighted goods, and the like. Medium temperature application can range from 61° C. to 600° C.

Activating Color Developing/Adhesive Layers and Compositions:

Solvent-based or other adhesive compositions can act as color developers directly with the color former to develop color without the use of ancillary or classic color developers. By way of example, but not limitation, aggressive adhesives including Tesafix™ 4965 (Tesa AG Quickbornstr, 24 D-20253 Hamburg Germany) and related adhesive tapes included, but not limited to Tesafix™ 4972. Admixes of low volatility solvents that may be suspended in or comprising polyacrylic acids and acrylic acid esters and the like can be used directly with color formers in the system described herein.

Tesa 4965 is a double sided adhesive tape consisting of a transparent polyester film and acrylic adhesive. The adhesive system is especially resistant to plasticizers and offers a secure bond even at elevated temperatures.

Main cited applications of Tesa 4965 include: mounting of ABS plastic parts in the car industry, self-adhesive mounting of rubber/EPDM profiles, mounting of decorative profiles and mouldings in the furniture industry, and mounting of battery packs, lenses and touch-screens in electronic devices. It was non-obvious that the commercially available adhesive tape could be used as a practical, low cost, and commercially available color development laminate.

4965 is an 8.1 mil, double coated adhesive tape consisting of a transparent polyester film with a red polypropylene release liner. The adhesive system is especially resistant to plasticisers and offers a secure bond even at elevated temperatures.

Polymeric Color Developers:

Polyacrylic acid and polyacrylic acid esters are of particular interest in their function as dual active adhesives and acidic characteristics that simultaneously can provide and assist as a color developer when directly reacted with color forming compositions.

A variety of small to large molecular weight polyacrylic acids (PAA) can be utilized. The molecular weight determination, degree of polymerization, mobility, proton donating characteristics, adhesive binding characteristics, melting point characteristics, phase transition, density, molecular weight cutoff, degree of chemical modification, associated binding resin and the like can be used as modification characteristics in the color development process.

Acrylic acid monomers, oligomers, low molecular weight polymers, medium molecular weight polymers, and high molecular weight polymers act as both adhesive constituents as well as polymeric color developers. Acrylic acid monomers to high molecular weight polymers greater in molecular weight than 50,000,000 g/mol can be utilized. Usually, oligomeric compounds ranging in molecular weight from 500 g/mol to 20,000,000 g/mol will find use. More usually, polymers from 1,000 to 10,000,000 g/mol in size will find dual uses as developers and adhesive components. Typically polymers from 2,500 to 5,000,000 will be most often used.

Adhesive Composition Components:

Adhesive composition components can find use including specialty tapes, repositionable tapes, packaging tapes, permanent labels, and peelablelrepositionable labels. Raw materials commonly used in these applications include hydrocarbon tackifiers, rosin esters, and resin dispersions. These products promote tack and enhance adhesion to low energy surfaces. Additional composition components can include surfactants, emulsifiers, thickening agents, stationary colorants, microspheres to promote removable adhesives, diluents, labeling agents, security tagging agents and the like.

Polymeric acidic compositions can be formulated alone or along with corresponding esters to form adhesive compositions with specified color development characteristics described. Solvents and tackifying agents will be added to the adhesive composition to provide pressure sensitive adherent properties to the color developing adhesive.

Solvents can include, but are not limited to aqueous solvents, organic solvents, low volatility organic solvents, and inorganic fluids. It is preferable to select a solvent system that provides for adequate adhesive properties, is low in volatility so that its properties are only nominally impacted with time and evaporation, serves to adequately solubilize the polymeric acid composition, and provides for mobility and interaction with in the color development system, but does not complicate or negatively impact he color development process.

Tackifiers are added to ensure pressure sensitive and immediate contact between the color development adhesive composition and the color forming substrate layer. By way of example, but not limitation, tackifiers can include carboxylated monoesters of polyglycols, etc. A wide range of solvent and water based tackifiers are commercially available and can be utilized in the time-temperature indicating system.

Polymeric binders of the adhesive can be chosen from a large series of polymers. Polymers can be soluble and/or alkali-soluble and compatible with the used tackifier. Suitable water-soluble and alkali-soluble polymers are e.g., polyvinylpyrrolidone, polyacrylic acid, polymethacrylic acid, copolymers of acrylic acid with alkyl esters of acrylic or methacrylic acid wherein the alkyl group comprises 1 to 4 carbon atoms such as methyl acrylate and n-butyl acrylate, with the proviso that the acrylic acid content is at least above 70% in the case of methyl acrylate and above 85% in the case of n-butyl acrylate, further copolymers of maleic acid and e.g. ethylene, vinyl methyl ether and vinyl acetate, dimethylhydantoin-formaldehyde resin and polyethylene imine.

The polymerization of acrylic acid and of methacrylic acid and the copolymerisation of these acids with lower alkyl esters of acrylic acid (methyl, ethyl, butyl) may be carried out in solution in water, in methanol or in mixtures of both according to known polymerisation techniques, e.g. according to the methods described in Houben-Weyl, "Methoden der organischen Chemie", Makromolekulare Stoffe, vol. 14/1, pages 1018-1021, Georg Thieme Verlag, Stuttgart (1961). Polymerisation may also occur according to known methods in a non-solvent, whereby the polymer formed precipitates out of solution. In the same way emulsion copolymerisation techniques may be applied when mixtures are used of acrylic acid or methacrylic acid with alkyl esters thereof, wherein the ratio of acid component is relatively low (30 to 55% by weight). The ratio of the amount of polymeric binder present to the amount of tackifier used can vary within very wide limits and depends among others on the relative humidity interval in which the adhesive tape is to be used. Best results are attained, however, when the amount of tackifier is from 100 to 280% by weight relative to the amount of polymeric binder present.

Tackifying Agents, Resins, and Matrices:

Hydrocarbon resins as tackifiers are comprised from petroleum based feedstocks either aliphatic (C5), aromatic (C9), DCPD (dicyclopentadiene), or mixtures of these. C5, aliphatic Resins are so named because they are generally polymers of monomers with five carbons. Basic C5 aliphatic resins have Gardner colors between 1.5 and 6 (from light yellow to light brown) and are mostly used to tackify aliphatic polymers, especially natural rubber, EVA, SIS and APO. Hydrogenated C5, Aliphatic Resins are basic C5 hydrocarbon tackifers that have been hydrogenated to improve their color and thermal stability.

C9, Aromatic Resins are so named because they are generally polymers of nine-carbon aromatic monomers. They are based on aromatic feedstocks that undergo very little refining prior to the polymerization of the resin. They are usually dark in color within typical Gardner color of 6 to 10 (dark yellow to dark brown). They are used mainly in EVA-based adhesives, contact adhesive for footwear, printing inks, sealants, and paints. C9 liquid resins are especially useful in flooring adhesives. As a class, C9 resins have a distinctive aromatic odor. There are two sub-categories of C9 aromatic tackifiers, each with distinctive properties.

Pure Monomer C9, Aromatic Resins are based on aromatic feedstocks that have been highly purified prior to polymerization. These are usually water-white with excellent stability. The lower softening point (<100° C.) types are mainly used in EVA for book binding adhesives and to improve creep resistance in HMA for diapers. The higher softening point pure monomer resin types are useful as end-block re-enforcers (enhance cohesive strength) in styrenic block copolymers, SIS, SBS, and SEBS.

Hydrogenated C9, Aromatic Resins are produced through the controlled hydrogenation of basic or pure monomer aromatic resins. A hydrogenated hydrocarbon tackifer resin is the best choice when color and stability are overriding concerns. Usually these resins are colorless (water-white) and are very stable to heat, weathering, and oxidation. Most are hypoallergenic, with no skin-sensitization properties and are ideally suited for adhesives used in the medical industry where these considerations are critical.

C5/C9, Aliphatic/Aromatic Resins are C5 tackifiers copolymerized with aromatic monomers. They are excellent tackifiers for use in EVA, SBS, and natural rubber polymers. They can also be used in SIS-based HMPSA to provide low melt viscosities with an optimum balance between cohesion and adhesion. Sometimes the slightly aromatic modified C5 resins are used in APO to provide limited compatibility resulting in shorter open times. Darker colored, lower cost types are often used in packaging HMA based on EVA. These resins are mostly C9-based co-polymerized with C5 aliphatic monomers.

The multiple element simultaneous characteristic of intimate adhesion, direct color development ability, time-delayed activity of color development, optical clarity, and ability to be tuned and modified chemically provide for a broad platform of application as a new class of color former/color developer systems described herein.

Alternatively, polymers containing acidic side chains comprising methacrylic acid, acryloyl chloride, acrylamine co-mixes, acrylate co-polymer admixes, sodium polyacrylate, propionic acid polymers, acryloyl groups, methacrylic acid derivatives, ethylacrylic acids can be utilized in addition to or in alone.

PAA can disperse the micro-crystals or micro-sand of calcium carbonate, calcium phosphate and calcium sulfate. Polyacrylic Acid is used as scale inhibitor and dispersant for circulating cool water system, papermaking, weave, dyeing, ceramic, painting, etc. polyglycolic acid polymer a synthetic biodegradable polymer, monomeric diacetylenes, polydiacetylenic acid polymers, monomeric and polymeric bisphenol A, butylated hydroxyanisole (BHA also used as an antioxidant) monomers and polymers there of, butylated hydroxytoluene (BHT), PAA based color developers can be dispersed, dissolved in, homogenized in, solubilized in, or combined with low volatility solvents such that the acid donating properties of the acidic side chains are available to participate in charge transfer characteristics of color development with a particular color forming composition comprising the adhesive time indicating system.

The addition of augmenting agents can be utilized to accelerate or decelerate the color development process. Accelerating agents can be comprised of compositions that facilitate the breakdown of encapsulation, semi-encapsulation, migration, or diffusion of one or both color developer or color former during a time and/or temperature monitoring event.

Decelerating agents can be comprised of compositions that facilitate the stability of encapsulation, semi-encapsulation, migration, or diffusion of one or both color developer or color former during a time and/or temperature monitoring event.

Accelerating agents can be added to a time and/or temperature indicating composition from between 0.01% to 90%. More often accelerating agents will be added between 0.1% and 50%. Usually accelerating agents will find use between 1% and 30% by weight in the final concentration in a time indicating composition.

Decelerating agents can be added to a time and/or temperature indicating composition from between 0.01% to 90%.

More often decelerating agents will be added between 0.1% and 50%. Usually decelerating agents will find use between 1% and 30% by weight in the final concentration in a time indicating composition.

The time-temperature dependent system described can utilize individual time dependent color development composition components and predetermined ratios provides for a wide range of performance capabilities for the system. Systems of interest can include one or more of the following components:

Color developer: (cd)
Color former: (cf)
Encapsulating composition: (ec)
Adhesive composition: (ac)
Accelerating agent (aa)
Decelerating agent (da)
Blocking composition: (bc)

Passive and Active Modulating Agents and Matrices:

Passive and/or active modulating agents and matrices can be used to offset, separate, control, modulate, accelerate, delay, attenuate, or predictably influence the interaction between color former compositions and color developer systems. The exact composition, thickness, concentration, and characteristic of modulating agent or substrate will depend on the application and/or desired effect intended for a particular application of interest.

Offset delay layers between the color former layer and the adhesive color development layer can be pressure actuated locally using a stylus, pencil or other pressure means such as a finger tip blunted object or sharpened object. The localized pressure can be used to induce a localized adhesion and localized initiation of the time or time-temperature dependent color development process. Messages can be written, dates applied, or other text or symbolic information noted and corresponding color developed as result of localized contacts.

Blocking and modulating layers can include, but are not limited to: chemical, physical, films, adhesive layers, wax layers, diffusion layers, porous layers melting layers, high viscosity layers and the like can be utilized to block ore delay the onset of color development as well as be used to great differential time delays compared with direct interaction between the color forming layer and the developing layer.

In addition to acting as carrier matrices, purified or complex compositions can act as a separation layer between the color forming layer and the associated color development layer. By way of example, a printed color-forming layer can be post coated with a hydrocarbon layer. The layer can act to delay the onset of color development when an activating adhesive or other color development layer is placed in intimate contact with the hydrocarbon layer juxtaposed to the color-forming layer. Color development can occur as the color development agent in the adhesive layer migrates through the layer and subsequently interacts with the color-forming layer to develop a color.

Passive and/or active modulating agents and matrices include, but not limited to waxes, acrylics, plastic resins, carboxy methyl cellulose (CMC), printing varnishes, hydrocarbon layers, nitrocellulose, paraffin, microcrystalline waxes, natural waxes, clay coatings, coating resins, tapes, non-developer containing adhesives, particulate, micro-particulate, thin metal layers, plastic film layers, dried protein layers, dried cellulosic layers, spray coated layers, surfactant layers, emulsifiers, membranes, semi-permeable membranes, filters, transparent layers, compliant layers, and the like.

Sharp melting point mediums, long chain amines, long chain carboxylic acids, long chain weak acid donors, charge carrying polymers, polymerize waxes, alkylated polymers, polyenes, polyolefins, polyethylene glycols, polypropylene glycols and a wide range of other passive or active matrices can be utilized in the resin system to achieve a suitable augmentation effect.

Clay coatings provide a protective, smooth printing surface on various substrates natural papers. The base paper—used for consumer packaging or printed marketing materials—must be coated to produce a surface that is bright white, opaque and smooth, with either a glossy or matte finish. This coating allows the base paper to receive high quality printing of text and graphics, without bleeding or smudging. Clay coatings can be purchased from commercial vendors (e.g. NuCoat Inc.)

Purified Hydrocarbon Carriers as Passive and Active Matrices:

Purified hydrocarbons, each of which can be used as a solvent to solublize monomeric color formers and yet not directly or on their own cause color development, can be selected as carriers that can affect the temperature transition associated with color development resulting from solvating a color former and a developing adhesive layer or agent. Purified hydrocarbon carriers include, but are not limited to chain lengths of C10, C11, C12, C13, C14, C15, C16, C18, C19, C20, C21, C22, C23, C24, C25, C26, C27, C28, C29, C30 and longer synthetic and/or naturally derived hydrocarbon chain lengths.

Similarly, longer hydrocarbon chain lengths can be used to mitigate color development at temperatures well below the melting transition of the hydrocarbon comprising the separation layer. Not until a threshold temperature above the melting or softening transition of the hydrocarbon layer along with the combined interaction of the adhesive composition will the color developing adhesive composition give rise to an association with the color forming layer and initiate color development.

Layer thicknesses can range from 0.1 micron to over 2 millimeters. Usually, layers find practical use in between 0.5 microns and 1 millimeter. More often, layers will range between 1 micron and 500 microns. Most often, layers are formed and used between 10 and 100 microns depending on the application of interest and time delay or color development onset delay of interest for a particular product application.

Microcrystalline Wax and Paraffin Bases for Color Former Dispersion:

Example High Melting Point Paraffins:

| Product Code | Melt Point (° F.) | Melt Point (° C.) |
| --- | --- | --- |
| IGI 1303A (AW5512) | 154 | 67.8 |
| IGI 1380A | 153 | 67.2 |
| IGI 1260A | 157 | 69.4 |

Example Mid Melting Point Paraffins:

| Product Code | Melt Point (° F.) | Melt Point (° C.) |
| --- | --- | --- |
| IGI 1239A | 138 | 58.9 |
| IGI 1240A | 136 | 57.8 |
| IGI 1242A | 139 | 59.4 |
| IGI 1245A | 140 | 60 |
| IGI 1250A | 142.5 | 61.4 |
| IGI 1302A (AW4212) | 140 | 60 |
| IGI 1343A | 138 | 58.9 |

Example Low Melting Point Paraffins:

| Product Code | Melt Point (° F.) | Melt Point (° C.) |
| --- | --- | --- |
| IGI 1230A | 130 | 54.4 |
| IGI 1236A | 132 | 55.6 |

Example Microcrystalline Waxes:

| | Melt Point ° C./° F. | Hardness @ 25° C. | Viscosity @ 100° C. | Color D1500/D156 | Packaged Forms |
| --- | --- | --- | --- | --- | --- |
| MICROSERE 5788A | 60/140 | 40 dmm | 19 mm$^2$/sec | L0.5/— | Slab |
| MICROSERE 5701A | 70/160 | 28 dmm | 14 mm$^2$/sec | L0.5/— | Slab |
| MICROSERE 5714A | 70/160 | 28 dmm | 14 mm$^2$/sec | L1.5/— | Slab |
| MICROSERE 5715A | 77/170 | 28 dmm | 16 mm$^2$/sec | —/+16 | Slab |
| MICROSERE 5799A | 77/170 | 28 dmm | 16 mm$^2$/sec | L1.5/— | Slab |
| MICROSERE 5818A | 83/181 | 18 dmm | 16 mm$^2$/sec | L3.5/— | Slab & Pellet |
| MICROSERE 5871A | 83/181 | 18 dmm | 16 mm$^2$/sec | L0.5/— | Slab & Pellet |
| MICROSERE 5890A | 83/181 | 18 dmm | 16 mm$^2$/sec | —/+16 | Slab & Pellet |
| MICROSERE 5981A | 84/183 | 14 dmm | 14 mm$^2$/sec | L0.5/— | Slab, Pellet & Granule |
| MICROSERE 5897A | 87/188 | 18 dmm | 20 mm$^2$/sec | L0.5/— | Slab, Pellet & Granule |
| MICROSERE 5896A | 87/188 | 18 dmm | 20 mm$^2$/sec | —/+16 | Slab, Pellet & Granule |
| MICROSERE 5901A | 89/192 | 9 dmm | 15 mm$^2$/sec | L0.5/— | Slab, Pellet & Granule |
| MICROSERE 5999A | 90/194 | 8 dmm | 20 mm$^2$/sec | L1.5/— | Slab, Pellet & Granule |
| MICROSERE 5909A | 90/194 | 8 dmm | 20 mm$^2$/sec | L0.5/— | Slab, Pellet & Granule |
| MICROSERE 5910A | 90/194 | 8 dmm | 20 mm$^2$/sec | —/+16 | Slab, Pellet & Granule |

Relevant Applications for Microcrystalline Waxes:

| Grade | Melting Point | Hardness | Applications |
| --- | --- | --- | --- |
| Type 1-Laminating | 54 to 76° C. | 20-35 dmm | Packaging Adhesives Cosmetics Rubber Candles |
| Type 2-Coating | 76 to 85° C. | 14-25 dmm | Adhesives Packaging Chewing Gum Inks Plastics Rubber |
| Type 3-Hardening | 85 to 95° C. | 6 to 14 dmm | Adhesives Inks Chewing Gum Candles Specialty |

Long Chain Alcohols as Color Former Carriers:

Unilin® Alcohols are available through Baker Hughes Inc., UNILIN alcohols feature than other commercially available linear alcohols. Compared with conventional alcohol technology that has been limited to carbon chain lengths of C30 or below, UNILIN Alcohols from Baker Petrolite are available with average chain lengths of C24 to C50. Melt points of UNILIN Alcohols products range from 78° C. to 106° C. Completely linear structure Fully saturated Higher molecular weights, Higher melting points, Greater crystallinity, and greater alcohol content UNILIN Alcohols are composed of approximately 80% primary alcohol; the remaining 20% is saturated or chemically inactive hydrocarbons of the same molecular weight. The hydroxyl function of the alcohol is evenly distributed among all carbon chain lengths. UNILIN alcohols from Baker Petrolite may be incorporated into a wide range of chemical processes and formulations. They offer improved compatibility with other high molecular weight functional polymers when compared to shorter chain alcohols or non-functional hydrocarbons. Features benefits of alcohol functionality include: Increased solubility in polar systems Co-emulsifier for silicones reactive sites for derivatives Linear carbon backbone: Compatible with hydrocarbons Solvent resistance in coatings Hard Controlled Mn (350-700) and narrow MWD: formulating flexibility Controllable melting point Low melt viscosity UNILIN® Alcohols from Baker Petrolite are incorporated as intermediates into a wide variety of industrial chemical processes and applications. Chemical intermediates for oxidation, sulfation, amination, and esterification: additives for adhesive formulations additives for coatings/paints and toners Lubricity improvers in plastics defoamer additives for pulp and paper systems compatibility enhancers for silicone systems Intermediate for polyester resins to reduce sensitivity to humidity Reversible/Irreversible Co-Development Indicating Present and Historical Temperature:

Reversible color developer/solvents such a glycerol monostearate can be utilized as a reversible color developer along to develop color in a color former type. In the absence of an irreversible color developer such as an aggressive adhesive layer the color generation process can proceed reversibly upon ascending temperatures. An irreversible color developer can be applied adjacent to or within the same indicating device or layer. During an ascending temperature event, the color development process will be irreversibly recorded in the presence of the irreversible color developer whereas reversible color development area will record only present time temperature conditions. The presence of both reversible and irreversible color development process simultaneously within the same device or indicator has the significant advantage of providing both historical temperature history as well as present temperature history utilizing the same color former system and developer elements.

Alternatively, descending color change dye compositions can be developed using the system described herein for irreversible or reversible temperature indication for development recording temperature histories where it is important to indicate whether a product had been exposed to a low temperature threshold in contrast to a high temperature threshold.

Activation of Time-Temperature Color Development Process:

Activation or initiation of the time and temperature dependent color development process begins upon intimate interaction of essential system components. Activation can be accomplished manually by applying a label containing one component to a substrate containing a second member. Both members are required for initiation and color development. In a second example activation can begin upon label application and contact between two members of the full color development pair by using automated labeling equipment.

Wrap around label applicators can be used for activation at the labeling point using labels constructed with one member of a color system on one surface and the other member on the opposing surface. During wrap around label application the bottom portion of a label will come in contact with the second member to initiate the color development process.

Pull tab activation finds use where semi-manual activation approaches are desired. A pull tab can be used to separate the two component color development system such that when the separation tab is pulled, the pulling process draws one layer member in intimate contact with the other layer member. Activation begins during the adhesion process.

Blocking layers can be utilized where by the blocking layer keeps dormant and maintains separation between two layer components until an elevated temperature or time is achieve. When a threshold temperature is achieved thereby melting or diffusing the blocking layer, both color former and color developer layer are allowed to interact and the color development process can proceed above the designated temperature or at any point where the blocking layer is eliminated.

Pressure initiated activation can be utilized whereby pressure is required to force on layer of a pair in direct contact with the second layer to induce intimate contact. Off-setting spacers can be used to separate one layer from the other. A gap can be placed between the two layers filled by only air or a displacing composition. As presser is placed on one layer, the second layer is forced to interact and initiate the color development process.

Blister packing constructs can be utilized where by on member of an activating pair can be placed distal to a second layer using a displacing plastic indented structure. As the indented structure is deformed or flattened, the deformation process forces both members of the color development pair to interact and initiate the color development process.

Bubble burst activation can be utilized whereby both members of a color development pair are separated by an air or gas pocket. Separation is disrupted by pressing and rupturing the bubble. An added sound effect can be elicited as an audio confirmation of initiating the color development process. Bubble separators can be further used to generate patterns during multiple adjacent ruptures. Advertising or promotional applications will find use as arrays of bubble activating patterns can be utilized.

Direct Thermal Label and Color Sensitive Medium Integration:

Completed constructs can be utilized whereby existing thermal papers, films, labels or substrates and carbonless papers, films, or substrates can be paired with an aggressive color developing adhesive described herein. Commercially available thermal substrates and carbonless substrates can be purchased and utilized in the system. Commercially available thermal substrates and carbonless substrates can be supplied by but not limited to: Appleton Papers Inc., Fuji Films Corp., Microtek Corporation, NuCoat Inc., NoCopi Technologies, Inc., Crayola Company, Elmers Inc., and Segan Industries, Inc., LCR Corp., TMC LLC, Rub and Color brand, Matsui Corp., Pilot Ink Crop., New Prismatic Corp., and other commercial providers of technical color change dyes and products.

As described in U.S. Pat. No. 4,822,770 carbonless copy paper is prepared by placing a first sheet of paper coated on one side with a hydrophilic colloid solution in which are dispersed microcapsules of oil droplets containing a colorless electron donor dye into contact with a second sheet of paper coated with an absorbent and an electron accepting color developer compound. The heat resistance and moisture resistance of the copy paper is substantially improved by adding to the hydrophilic colloid solution a graft copolymer having a backbone of carboxymethyl cellulose or gum arabic and side chains of polyacrylic acid or polymethacrylic acid. The image response time of the second sheet can be improved by adding pectin or sulfated starch to the coating. Substrates such as these can be utilized in combination with aggressive color developing adhesives to unexpected create time and time-temperature indicators.

Likewise, adhesive color development laminates can be utilized to adjust the intended color development threshold of existing direct thermal labels. By way of example, but not limitation, commercially existing direct thermal label substrates including paper and plastic film types, can be up-shifted in temperature or down shifted. Up-shifting can be accomplished by increasing the threshold properties of the direct thermal composition (e.g. inducing a localized differential base or acid change into the direct thermal composition. Downshifting the temperature transition of a direct thermal label composition can be accomplished both by an acid/base change locally as well introducing an increased mobilization and salvation property in the direct thermal composition.

Direct thermal papers and films most readily adjusted will be those with thermal compositions and coating amenable to localized changes that can be introduced by introduction and interaction of the adhesive overlay. The intended up-shift or downshift in thermal characteristics of the direct thermal transfer substrate will depend on the intended application of interest, the degree of temperature change intended and the time intended for introducing and optical change in the substrate.

Similarly, a commercially available direct thermal coated substrate can be converted into a time only indicating substrate depending upon the thermal coating composition and provided protective coating. By adjusting the aggressive nature of the adhesive overlay, the solvent content, the acid/basic nature of the adhesive employed and any intended augmenting agents comprising the adhesive composition, application of the adhesive laminate can be utilized for conversion of the substrate to shorter or longer duration time indicators.

Example direct thermal recording substrates available and useful from Appleton Papers Inc. include:

| | |
|---|---|
| 3802-0221 | RESISTE 600-4.4 8 7/8 5M |
| 2137-0036 | RESISTE 200-3.1 61 9M |
| 4723-0086 | RESISTE 500-3.4 9 1/2 1M |
| 4723-0044 | RESISTE 500-3.4 9 1/4 9M |
| 3802-0227 | RESISTE 600-4.4 7 6M |
| 3802-0080 | RESISTE 600-4.4 40 1/2 4.5M |
| 4723-0051 | RESISTE 500-3.4 13 5/16 6M |
| 3802-0182 | RESISTE 600-4.4 13 13/32 9M |
| 4211-0016 | RESISTE 800-7.2/T954 17 6.5M |
| 4723-0092 | RESISTE 500-3.4 8 3/4 9M |
| 3802-0224 | RESISTE 600-4.4 13 19/32 4.85M |
| 2137-0018 | RESISTE 200-3.1 27 9M |
| 3802-0043 | RESISTE 600-4.4 13 3/8 6M |
| 3802-0254 | RESISTE 600-4.4 19 7/8 7M |
| 3802-0195 | RESISTE 600-4.4 19 1/2 9M |
| 3802-0007 | RESISTE 600-4.4 13 1/2 9M |
| 3802-0247 | RESISTE 600-4.4 10 3/4 7.778M |
| 3802-0167 | RESISTE 600-4.4 16 1/2 1M |
| 2137-0026 | RESISTE 200-3.1 10 .5M |
| 3802-0256 | RESISTE 600-4.4 16 15/16 9M |
| 4723-0058 | RESISTE 500-3.4 9 1/2 6M |
| 3802-0145 | RESISTE 600-4.4 26 7/8 6M |
| 4723-0042 | RESISTE 500-3.4 16 1/2 9M |
| 4723-0002 | RESISTE 500-3.4 24 1/2 6M |
| 3802-0142 | RESISTE 600-4.4 5 3M |
| 3802-0151 | RESISTE 600-4.4 13 1/2 6M |
| 3802-0138 | RESISTE 600-4.4 5 4.5M |
| 3802-0000 | RESISTE 600-4.4 |

-continued

| | |
|---|---|
| 3802-0130 | RESISTE 600-4.4 4 ¾ 4.5 |
| 3802-0065 | RESISTE 600-4.4 12 ¼ 6M |
| 2137-0022 | RESISTE 200-3.1 50 6.667M |
| 4723-0087 | RESISTE 500-3.4 39 ¼ 9M |
| 4723-0003 | RESISTE 500-3.4 48 1/2 6M |
| 3802-0106 | RESISTE 600-4.4 13 1M |
| 4211-0024 | RESISTE 800-7.2/T954 13 1M |
| 2137-0028 | RESISTE 200-3.1 53 ¼ 9M |
| 4211-RL | RESISTE 800-7.2/T954 |
| 3802-0116 | RESISTE 600-4.4 15 4.5M |
| 3802-0238 | RESISTE 600-4.4 5 ¹³⁄₁₆ 6M |
| 3802-0250 | RESISTE 600-4.4 16 ¾ 5.2M |

| Part Number | Description |
|---|---|
| 7041-SH | 62 C1S PEARLESCENT LABEL |
| 3609-SH | C1S CREAM LABEL |
| 3659-0087 | T1062A OPTIMA LABEL 40" 9M |
| 3796-RL | C1S PK FLUOR LABEL |
| 4946-RL | BASE-COATED LABEL STOCK-13 CM |
| 7377-0000 | BLADE COAT THERMAL LABEL |
| 0000-3909 | C1S #270 CRM LABEL 25 × 38 |
| 3659-0033 | T1062A OPTIMA LABEL 30 ¾" 6M |
| 3659-0065 | T1062A OPTIMA LABEL 40" 6M |
| 4946-0001 | BASE-COATED LABEL STOCK-13 CM |
| 3659-0063 | T1062A OPTIMA LABEL 8 ½" 6M |
| 3608-0009 | C1S CAN LABEL 38 × 50 |
| 3659-0101 | T1062A OPTIMA LABEL 60 ¾" 9M |
| 3659-0015 | T1062A OPTIMA LABEL 53" 4.5M |
| 5194-0001 | BARRIER LABEL 62#FDA 20.5 × 23.5 |
| 7041-0000 | 62 C1S PEARLESCENT LABEL |
| 3608-0000 | C1S CAN LABEL |
| 7377-RL | BLADE COAT THERMAL LABEL |
| 3608-RL | C1S CAN LABEL |
| 3659-0128 | T1062A OPTIMA LABEL 60 ¾ 12M |
| 3659-0169 | T1062A OPTIMA LABEL 52" 12M |
| 3659-0155 | T1062A OPTIMA LABEL 24" 3M |
| 3610-RL | C1S IVORY LABEL |
| 3659-0119 | T1062A OPTIMA LABEL 13" 9M |
| 3823-RL | SC SP TAN LABEL |
| 3608-0010 | C1S CAN LABEL 25 × 38 |
| 3659-0165 | T1062A OPTIMA LABEL 61" 9M |
| 3796-SH | C1S PK FLUOR LABEL |
| 3796-0000 | C1S PK FLUOR LABEL |
| 0000-1227 | 150 AP LABEL PLT 61" 9.666M. |
| 4946-0000 | BASE-COATED LABEL STOCK-13 CM |
| 3801-SH | C1S SP BUF LABEL |
| 3659-0034 | T1062A OPTIMA LABEL 38 ⅝" 9M |
| 7041-RL | 62 C1S PEARLESCENT LABEL |
| 0000-2711 | C1S 259 GLD AP LABEL 26 × 20 |
| 3801-RL | C1S SP BUF LABEL |
| 5021-0001 | GENDATA LABEL-2.1 53 3M |
| 3609-RL | C1S CREAM LABEL |
| 3659-0105 | T1062A OPTIMA LABEL 26 ½" 6M |
| 3659-0085 | T1062A OPTIMA LABEL 61 ¼" 9M |

Time based color development process for devices, sensors, and products described above can range from seconds to years depending on the intended application of interest, compositions comprising said devices, delay layers employed and the like. Usually, time based applications will range from minutes to months. More usually, intended applications will utilize compositions and constructs that will give an observable color development in the range of hours to weeks.

Spot Color Developing Adhesives:

Printable spot color development adhesives were can be prepared using color developing polymeric and non-polymeric color developers, tackifying compounds, and ancillary binding agents and resins. Spot printed adhesives have the advantage over flood coated adhesive in making time and time temperature indicating constructs in that the spot adhesive can be selectively printed, pattern, and positioned in selective areas for desired and enhanced effects. Likewise, printed spot adhesives comprising color decaying compositions can be formulated using basified compositions under similar means.

Time-Temperature and Temperature Thermometers:

Visual read thermometers and sensors can be produced using time-temperature and time based color forming and color developing compositions. Constructs comprising thermometers can include a color forming layer on a substrate, a delay or temperature responsive blocking layer, and a pre-adhered color developing layer. The selection of components can be used to pre-set the time-temperature and temperature triggering temperature threshold of the thermometer.

In particular, the blocking layer positioned between the color forming layer and the adhered color developing layer can be formulated with a blocking compound that responds to and transforms to a permeable layer at a specified temperature. By way of example, the blocking layer may be a sharp melting point medium such as a wax, paraffin, or other commercially available sharp melting point medium. Upon melting, softening, or becoming permeable, the blocking layer will no longer be able to block or inhibit interaction between the color development system and an irreversible color will develop at the pre-determined temperature setting.

A time-delay can be introduced into the thermometer by adjusting the diffusion path, permeability characteristics of the blocking layer, composition of the color forming layer, and composition of the color developing layer. Time delays will typically be in the shorter duration stages from less than a second to several hours. More often time delays well be utilized in the range from a few seconds to an hour depending on the application of interest.

Thermometers can be produced to using the system to measure temperatures ranging from sub-freezing to over 1,000° C. Usually, temperature range will be in the freezer range starting at −5° C. and cover ranges in cooking and product preparation ranges up to 500° C. More often temperature ranges for thermometers will find use in the refrigerator range from 10° C. to 250° C.

Reversible Re-Activation Using Color Eliminating Systems:

Microencapsulated reversible leuco dye compositions can be converted to irreversible time and or temperature monitoring compositions utilizing irreversible adhesives or compositions that irreversibly attack and break down the microencapsulating side wall of the encapsulated species containing a color former.

Graphics and Messaging:

Messages, symbols, illustrations, titles, graphics, text, text messages, messages in general, images, icons, licensed figures, numerical values, hidden messages, line art, detailed art, multi-colored images, embedded graphics, graphic elements or entire graphics, visual que's, obscured images, partial images, pricing information, security information, promotional information, safety information, marks, patterns, and the like can be combined with time and time-temperature color development processes and compositions described above.

Graphic and messaging information can be printed with stationary inks above or below the time and time-temperature development compositions. Graphic and messaging information can be printed with time and time-temperature inks and combined with stationary graphics and messages. Likewise, both stationary and time-temperature inks can be combined in unique ways to generate messages that appear and disappear.

Graphic overlay patterns can be employed whereby the graphic overlay obscures an a color developing graphic or message comprised of the time or time temperature ink composition. As the time or time temperature ink develops in the initial stages, it is obscured by the stationary graphic overlay pattern until development proceeds to an intensity that the developing ink becomes discernable through the graphic overlay pattern.

Alternatively, a developing graphic or image comprising the developing ink can be printed in a trapped pattern that is compatible or continuous with the developing ink. Initially, the message is apparent. As the developing ink continues to develop, it will become similar in pattern, hue, and intensity with the stationary graphic. At a pre-described time or time-temperature profile, the developing pattern color and pattern matches the stationary pattern and becomes indiscernible against the background and the message or graphic appears to disappear.

A wide range of graphic and messaging formats can be utilized to emphasize, obscure, confuse, re-register, change, morph, transition, alter, become apparent, alter, integrate or the like to achieve a desired result that best suit the readout or resulting effect intended for a particular product application of interest. Examples stated above are cited by way of emphasizing a wide range of options, but not intended as limitations.

Conversion of AFM to High-Resolution Thermal Printing System Using Printed Dye Systems:

AFM with a heater tip can be utilized for high resolution color development based upon differentiated RGB color change pigments. Full color image development based on high resolution marking through selective identification of pigment particles even though particles are randomly printed.

Integration of Visual Time and Time-Temperature Compositions and Constructs into Microelectronic Recording Devices:

Microelectronic time and time-temperature devices capable of recording historical and/or real time histories of temperatures over time benefit from integration of visual time and time-temperature indicating systems described herein by providing in addition to electronic readouts, visual indications directly on the recording device or label.

By way of example, but not limitation, time and/or temperature indicating regions can be integrated with microelectronic heating elements and/or flash imaging circuits that are powered and tripped by the microelectronic device during a time or time-temperature recording session. The heating element can be used to develop a localized temperature high enough to irreversibly trigger a color change in the juxtaposed irreversible thermochromic layer.

The combination of a microelectronic digital historical data set and a visual color change element provides users of the device with a novel option of visualizing immediately whether a temperature threshold had been breached along with a historic data recording of the time and temperature history of a product that the integrated device had been attached to.

Reversal of Pre-Colored/Triggered Compositions as Time and Time Temperature Indicating Compositions and Articles:

Pre-colored/triggered color former and color developer compositions can be printed on amenable substrates including papers, films, and other convenient mediums for product formats. Pre-colored donor/acceptor complexes can be dissociated using mild basic mediums. Mild basic mediums can be delivered to the pre-colored/triggered complexes by a variety of means including adhesive compositions comprising a basic composition that can intimately interact over time and/or temperature parameters to change the colored complex to a non-colored medium.

Alternatively and by way of example, but not limitation, a basic ink composition can be marked or printed onto the pre-colored composition to deliver a metered amount of neutralizing medium and thus reverse the color to a colorless state. The color decay process can be correlated over time and time temperature to generate indicating devices that can serve as alternative time indicating sensors, time-temperature sensors, and temperature monitoring sensors. Methods described herein for blocking, acceleration, product embodiments, processes and the like for color generating process can be readily utilized as practical means to enable the color decay process A wide range of commercially available marking inks including fluorescent inks, resins, dyes, liquid concentrates, marking pens, fluorescent markers, basic glues, glue sticks, emollients, gels, basic adhesive tapes, basic pressure sensitive labels, pressure sensitive adhesive compositions, ink-jet inks, and a variety of related or alternative mediums for delivering a metered amount of basic medium to stimulate color reversal for a time or time temperature dependent indicating process can be employed.

Color generated color forming/color developing compositions can be pre-colored using various stimuli including co-solvation, aggressive mixing, frictional mixing, co-melting, and the like. The pre-colored complex of a donor and acceptor can be readily formulated as an ink or coating. Pre-coloration can also be process post printing through treatments described above. Subsequently, the color decay processes herein can be employed as a time and time temperature indicating means.

Spot Color Decaying Adhesives:

Printable spot color development adhesives were can be prepared using color decaying basic compositions, tackifying compounds, and ancillary binding agents and resins. Spot printed adhesives have the advantage over flood coated adhesive in making time and time temperature indicating constructs in that the spot adhesive can be selectively printed, pattern, and positioned in selective areas for desired and enhanced effects. Of interest are commercially available color decaying compositions, Fluorescent makers, sunscreen stick (Banana Boat), etc.

Buffering Agents and Capacities:

A buffer solution is an aqueous solution consisting of a mixture of a weak acid and its conjugate base or a weak base and its conjugate acid. It has the property that the pH of the solution changes very little when a small amount of acid or base is added to it. Buffer solutions are used as a means of keeping pH at a nearly constant value in a wide variety of chemical applications.

A wide range of buffering solutions can be employed to assist in the regulation of color forming and color decaying applications. Buffering compositions can include, but are not limited to: phosphate buffering, PBS, tris-buffers, and like. Useful buffer mixtures are listed below:

| Components | pH range |
|---|---|
| HCl, Sodium citrate | 1-5 |
| Citric acid, Sodium citrate | 2.5-5.6 |
| Acetic acid, Sodium acetate | 3.7-5.6 |
| $Na_2HPO_4$, $NaH_2PO_4$ | 6-9 |
| Borax, Sodium hydroxide | 9.2-11 |

"Universal" buffer mixtures are summarized below. By combining substances with $pK_a$ values differing by only two or less and adjusting the pH a wide-range of buffers can be obtained. Citric acid is a useful component of a buffer mixture because it has three $pK_a$ values, separated by less than two.

The buffer range can be extended by adding other buffering agents. The following two-component mixtures have a buffer range of pH 3 to 8.

| 0.2M Na$_2$HPO$_4$/mL | 0.1M Citric Acid /mL | pH... |
|---|---|---|
| 20.55 | 79.45 | 3.0 |
| 38.55 | 61.45 | 4.0 |
| 51.50 | 48.50 | 5.0 |
| 63.15 | 36.85 | 6.0 |
| 82.35 | 17.65 | 7.0 |
| 97.25 | 2.75 | 8.0 |

A buffering agent adjusts the pH of a solution. The function of a buffering agent is to drive an acidic or basic solution to a certain pH state and prevent a change in this pH. Buffering agents have variable properties—some are more soluble than others; some are acidic while others are basic. As pH managers, they are important in many chemical applications, including agriculture, food processing, medicine and photography.
Temperature Dependent pKa Compositions for Regulation:

An acid dissociation constant, $K_a$, (also known as acidity constant, or acid-ionization constant) is a quantitative measure of the strength of an acid in solution. It is the equilibrium constant for a chemical reaction known as dissociation in the context of acid-base reactions.

$$HA = A^- + H^+$$

where HA is a generic acid which dissociates by splitting into A$^-$, known as the conjugate base of the acid, and the hydrogen ion or proton, H$^+$, which, in the case of aqueous solutions, exists as a solvated hydronium ion. In the example shown in the figure, HA represents acetic acid, and A$^-$ the acetate ion. The chemical species HA, A$^-$ and H$^+$ are said to be in equilibrium when their concentrations do not change with the passing of time.

EXPERIMENTAL

I. Color Former/Color Developer Compositions
A. Reversible Color Development Hydrochromic Inks:
A pre-colored reversible hydrochromic ink is prepared using a two component solution mixture containing developer and color former. The developer solution is prepared using 10% by weight developer (Pergafast 201, Ciba AG CH) dissolved in 90% polyethylene glycol average molecular weight 1,450 g/mol (Sigma Chemicals). The mixture is brought above 200° F. and mixed until the solution becomes clear. A color former solution is prepared using 20% by weight color developer Specialty Magent 20 (Emerald Hilton Davis, LLC) dissolved in 80% by weight polyethylene glycol average molecular weight 1,450 g/mol (Sigma Chemicals). The mixture is brought above 200° F. and mixed until the solution becomes clear.

The developer solution and color former solutions are kept heated mixed. A slight magenta color develops. The solution is allowed to cool to 160° F. 3 volumes of hot water (greater than 160° F.) is added during vigorous mixing. An immediate magenta colored emulsion is formed and the solution is allowed to thicken during cooling to room temperature. The concentrated slurry may be removed for addition to an ink vehicle or used directly as a coating ink.
B. Reversible Color Development Hydrochromic Papers:
An aqueous slurry ink is coated on standard white bond paper. The coating is warm air dried. The initially colored—hydrated ink is converted to a colorless state during drying. Drying and conversion to a colorless state may be facilitated using forced warm air.

Color markings, drawings, graphics, message writing, symbols and the like may be generated buy applying a water marker, pen, swab, stamp to the colorless coated area of the paper. Colors generated by contact with water are observed to dissipate within minutes upon drying. The color development and color dissipation is reversible over a large number of applications.
C. Reversible Color Development Composition Based on Ascending Temperature:
A simplified and intense ascending reversible color development coating composition is prepared using a novel single component phase separating color developer and a single component color former. 83% by weight of a ascending color developer glycerol monostearate (2,3-dihydroxypropyl C18, GMS) is heated to 180° F. to ensure complete melting and low viscosity. 17% by weight green color former (Pergascript™ green I-2GN, Ciba AG CH) is added as a powder, mixed and heated (>180° F.) until completely dissolved. The color former is observed to turn deep green as it dissolves to a rich dark green mixture. The mixture retains a deep green color provided that it remains molten. Cooling to room temperature results in a transition of the formulation to an off-white slightly tinted waxy solid.
D. Reversible Ascending Temperature Color Development Substrates:
A reversible ascending temperature color change substrate is prepared using the reversible color development composition prepared in Example C. A solidified room temperature composition is heated to 160° F. until it is deep green and molten. The molten composition is then applied to paper substrates by a variety of standard coating processes. For convenience, the composition is roller coated on a standard 80 pound bonded white paper. Rollers are pre-warmed to ensure even coating.

Uniform coatings are applied to paper substrates. The coatings cool rapidly at room temperature (68° F.). Initially colored coatings turn from a deep green coloration to a translucent off white color upon cooling. The coating penetrates well into the paper substrate providing good stability on the paper. Cooled non-colored coatings are changed from colorless state to a colored state upon raising the temperature above the melting transition of the ascending color developer glycerol monostearate. The color completely reverses upon cooling back to room temperature. The ascending color change is reversible over continued repeated cycles and long term storage.
E. Micro-Encapsulation of Reversible Color Development Compositions Base on Ascending Temperature:
An ascending reversible color development coating composition is prepared using a novel single component phase separating color developer and a single component color former is prepared in accordance to Example C above. 83% by weight of a ascending color developer glycerol monostearate (2,3-dihydroxypropyl C18, GMS) is heated to 180° F. to ensure complete melting and low viscosity. 17% by weight green color former (Pergascript™ green I-2GN, Ciba AG CH) is added as a powder, mixed and heated (>180° F.) until completely dissolved. The color developer turns deep green as it dissolves to a rich dark green mixture. The mixture retains a deep green color provided that it remains molten.

The mixture is homogenized and dispersed in an aqueous medium until the average particle size is 2 microns. The color former dispersion is then admixed by stirring first with a 70% strength by weight aqueous solution of melamine-formaldehyde resin (molar ratio of melamine:formaldehyde 1:6) and a 20% strength by weight aqueous solution of polyacrylamidomethylene-propanesulfonic acid in a weight ratio of 1:1 and subsequently with a normalizing amount of sodium dihydrogenphosphate. The mixture is then adjusted with formic acid to pH 4.2. After mixing at room temperature for one hour and the addition of 2.5 g of water, the mixture is stirred at 160° F. for 2 hours until curing was complete.

A micro-encapsulated slurry is obtained in approximately 30-40% by weight aqueous dispersion of ascending reversible color generating reverse leuco dye which is colorless at room temperature and becomes reversibly intensely colored above the melting transition of the co-developer/solvent GMS.

The micro-encapsulated composition subsequently is either separated and dried to a powder form to be admixed to non-aqueous printing vehicles such as UV curable ink resins or solvent based in resins or is used directly as an additive to aqueous slurry to be added to aqueous based printing vehicles.

F. Separate Reversible Red, Blue, and Green (RGB) Color Development Compositions Based on Ascending Temperature for Color Image Development:

Color enriched ascending reversible color development coating compositions are prepared using a novel single component phase separating color developer and a single component color formers. 80% by weight of an ascending color developer glycerol monostearate (2,3-dihydroxypropyl C18, GMS) is heated to 180° F. to ensure complete melting and low viscosity. 20% by weight either red, blue, or green color formers (Pergascript™, Ciba AG CH) are added as powders, mixed and heated (>180° F.) until completely dissolved. The color formers turn deep independent colors as they each dissolve. The mixtures retain a deep red, blue or green color provided that they remain molten. Cooling to room temperature results in a transition of the formulation to an off-white slightly tinted waxy solid.

Each RGB color development composition is utilized in a 3-color printing process to generate a realistic color image. The initial printing processes require careful plate positioning to ensure color registration. Color printing is accomplished while the color development compositions are elevated in temperature and in the colored state. Upon cooling to room temperature, the image disappears on the paper printing substrate. As the substrate is warmed, the image appears from a blank page reversibly until the page is cooled again back to room temperature. The reversible ascending temperature effect provides an unusual an unexpected image development process as compared to standard available leuco dye compositions that can only be used to reveal an underlying image.

G. Separate Reversible Red, Blue, and Green (RGB) Color Development Compositions and Generation of Hydrochromic Full Color Image Development:

Color enriched hydrochromic reversible color development coating compositions are prepared using novel color former/developer compositions. Pre-colored RGB reversible hydrochromic inks are prepared using independent two component solution mixtures containing developer and color former as described in Example I. The developer solutions are prepared using 10% by weight developer (Pergafast 201, Ciba AG CH) dissolved in 90% polyethylene glycol average molecular weight 1,450 g/mol (Sigma Chemicals). Each mixture is brought above 200° F. and mixed until the solution becomes clear.

Separate color former solutions are prepared using 20% by weight color developer Specialty Red, Specialty Blue, or Green (Emerald Hilton Davis, LLC) dissolved in 80% by weight polyethylene glycol average molecular weight 1,450 g/mol (Sigma Chemicals). The mixture is brought above 200° F. and mixed until the solution becomes clear.

Corresponding color developer solutions and color former solutions are kept heated mixed and kept independent. Slight colors are developed upon mixing. The solutions are allowed to cool to 160° F. 3 volumes of hot water (greater than 160° F.) are added during vigorous mixing. An immediate red, blue or green colored emulsion is formed and the solutions are allowed to thicken during cooling to room temperature. The concentrated slurries can be removed for addition to an ink vehicle or used directly as a coating ink.

The aqueous slurry inks are printed in RGB patterns on standard white bond paper. The coating is warm air dried. The initially colored—hydrated ink is converted to a colorless state during drying. Drying and conversion to a colorless state are facilitated using forced warm air.

Full color images, multi-colored markings, drawings, graphics, messages writing, symbols and the like can be generated by applying a water marker, pen, swab, or stamp to the colorless coated area of the paper. Colors generated by contact with water are observed to dissipate within minutes upon drying. Color image development and color dissipation are reversible over a large number of applications.

H. Coacervation Micro-Encapsulation of Reversible Color Development Compositions for Ascending Temperature Color Change Dyes:

150 ml 8% aqueous solution of 200 Bloom Type A Gelatin at 50° C. is combined together with 0.1 ml of n-octanol as a foam suppressant. 80 gm of 2,3-glycerol monostearate is pre-mixed with 20 gram color former Pergascript™ orange 1-G (Ciba AG CH) and then mixed into the aqueous solution with agitation to form oil phase droplets in the range of 10-20 microns. The emulsion pH is adjusted to pH 5. 10 ml of a 28% solution of sodium polyaspartate diluted with an additional 40 ml of water is added to the emulsion during mixing. An additional 170 ml of distilled water is subsequently added. The pH of the mixture is then lowered to 4.4 by addition of glacial acetic acid. The mixture is cooled to about 10° C. and the pH lowered to pH 4.2. The solution is allowed to cool 45 minutes at 10° C. whereby 0.5 ml of a 25% glutaraldehyde solution is added and the mixture allowed to stay 12 hour at 22° C.

The micro-encapsulated composition is subsequently either separated and dried to a powder form to be admixed to non-aqueous printing vehicles such as UV curable ink resins or solvent based in resins or is used directly as an additive to aqueous slurry to be added to aqueous based printing vehicles.

I. Natural Co-Developer-Solvent Based Leuco Dye Compositions:

A natural co-developer-solvent leuco dye is prepared by pre-melting 80% carnauba wax to 100° C. Color former is added at 20% by weight and mixed. The mixture is heated and mixed until the color developer is completely dissolved into a clear molten solution. The molten solution is allowed to cool to room temperature. Upon cooling the composition is solidified to a rich deep color. The solidified colored composition exhibited fully reversible color change characteristics upon heating and melting and chilling and solidification. The solidified composition could be used directly as a coating or converted to a powdered form for addition to printing vehicles, plastics extrusion compositions, injection molding compositions or the like.

J. Aqueous Coating and Product Additive Slurries Using Natural Co-Developer-Solvent Based Leuco Dye Compositions:

Aqueous slurries of natural co-developer-solvent based leuco dye compositions prepared as described in Example I above are emulsified using food-grade surfactants and ultra-sonication. A 20% by weight emulsifier solution of Protanal Ester BV 3750 (FMC Biopolymer) is prepared by adding amd mixing the surfactant in stirring water at 70° C. until the emulsifier is completely dissolved. 50% by weight natural co-developer-solvent based leuco dye compositions are heated to a liquefied state (100° C.). 50% by weight pre-heated emulsifier solution is added and the mixture is sonicated using a 300 watt ultrasonicator probe. A uniform slurry emulsion is formed within 2 minutes of sonication. The slurry is allowed to cool to room temperature. The slurry may be used directly as a coating ink or utilized at various concentrations as an additive to ink vehicles. Pre-formed slurries can be further mico-encapsulated using standardized micro-encapsulation processes describe above.

K. Leuco Dye/Polydiacetylenic Combinatorial Compositions in which Diacetylenic Moieties Serve as Color Developers and Possess Intrinsic Color Change Polymer Characteristics:

10% by weight color formers—either red, blue, or green (Pergascript™, Ciba AG CH) and 10% by weight 10,12-tricosadiynoic acid (C23) are dissolved is dichloromethane. The presence of the free monomeric C23 acid initiates color development in solution. The solutions are tinted relative to the color type. Each formulation is dried on to paper. The resulting colors are rich in hue. Each color type exhibits a reversible color change when elevated above 160° F.

Dried color draw-downs are subsequently exposed to UV light (254 nm) resulting in the formation of an additional blue hue to each color type exposed. The blue hue is generated by the topochemical polymerization reaction forming the ene-yne polydiacetylenic polymer backbone. The blue hue may be irreversibly changed to a red hue during heating or through frictionally induced mechanochromic triggering. The leuco dye reversible color change is convoluted with the polydiacetylenic color transition.

L. Solvent Based Compositions for Inkjet, Drop-on-Demand, and Continuous Inkjet Printing:

10-15% by weight color formers and developers are dissolved in solvent systems including ratios of chloroform, methylethyl ketone, and alcohol types. Soluble resins such as polyethylene glycol and other soluble, but adherent polymers may be used. Soluble solutions are used directly as printing ink compositions in various inkjet, drop-on-demand, and continuous inkjet printing formats.

M. Developers Comprising One Adhesive Layer can be Adhered to Standard Thermal Printing Paper to Develop a Time Dependent Image:

Developers comprising adhesives used in tapes and pressure sensitive labels are contacted with commercially available and standard thermal printing used for printing paper receipts at checkout. Color is developed in the thermal printer based on the developer migrating from the adhesive layer to the color former layer in the thermal paper. Further, the adhesive may be selectively patterned to generate images that develope as time progresses after contacting the patterned adhesive layer with the color development layer.

N. A Developer Comprising One Component of a Printed Layer and a Color Developer Comprising a Second Component is Color/Time Activated Using a Slow Migrating Adhesive/Solvent:

A micro-encapsulated developer and color former are co-printed such that no color is developed after printing had been accomplished. The slow migrating solvent effect of an adhesive layer acts to dissolve the encapsulation layer from the developer thereby releasing the developer to initiate a color change in the color former. Further adhesive may be selectively patterned to generate images that develop as time progresses after contacting the patterned adhesive layer with the color development layer.

O. Compositions of the Invention Find Use in a Variety of Different Applications, Including but not Limited to:

Novel color development for cold chain management:
Ascending temperature indicator as color is develops
Ascending temperature indicator where color development lock occurs at set points:
Shunted color development dependent on time along one axis and temperature along another:
Site addressable flash imaging using ascending temperature leuco dyes:
3D flash imaging using ascending temperature leuco dye:
Message that appears as color develops rather than ink opacity changing to make message appear:
Reversible color development candles:
Reversible color development printable dyes:
Irreversible color development thermal inks and papers:
Toys applications that turn color upon touching:
Ascending temperature indicating composition for lotions and emollients:
Physiologic temperature status determination devices:
Hydration indicating composition for lotions and emollients to determine physiologic hydrations status:
Developers that co-act as alternative active agents e.g. flavors, fragrances, stimulants:
Long-term hysteresis effect and reversal using water reactivation based on aqueous slurry inks:
Long-term hysteresis effect and reversal using heat reactivation based on aqueous slurry inks:
Novel flexographic in-line layering/manufacturing as a production means for tunable color indicating systems:
Ultra sharp critical melting point mediums for digital color development:
Ascending reversible color development leuco dye
Ascending reversible color development leuco dye with hysteresis
Temperature adjustable ascending color development leuco dye
Micro-encapsulated ascending color development leuco dye
Co-solvent-developer single component molecule
Hydrochromic reversible color development leuco dye
Mixed ascending and descending reversible leuco dyes
Natural co-developer-solvent for ascending color development
Natural co-developer-solvent for descending color development
Single component as dual solvent and color developer properties
Slurry concentrates of natural ascending and descending leuco dyes
Leuco dye color formers—developed by polydiacetylenic developers
Reversible color to colorless based on temperature
Reversible colorless to color based on temperature Reversible color to colorless based on hydration
Reversible colorless to color based on hydration
Reversible color to colorless based on solvation
Reversible colorless to color based on solvation
Irreversible colorless to color based on temperature
Irreversible color to colorless based on solvation
Reversible non-hysteresis color change
Reversible color change with hysteresis types
Irreversible non-hysteresis color change
Irreversible color change with hysteresis types II. Time and Time-Temperature Examples A. Color Referenced Time and Time Temperature Sensors Using Pre-Mixed Color Forming Compositions and Activating Adhesives:

Pre-mixed color forming compositions and inks are utilized as time and time temperature indicating systems in combination with activating adhesives. 60° C., 75° C., 90° C. and 100° C. irreversible thermochromic ink compositions (Kromagen and/or Kromax concentrate, Thermographic Measurement Co.) are flexographically printed using a 20 anilox roller on various paper and film stocks (pressure sensitive and non-pressure sensitive stock types). Magenta, orange, cyan, blue, turquoise, green, black and red color types are printed.

Labels are die-cut in-line. Reference color graphics are simultaneously printed in-line using color hues and intensities calibrated as reference colors for given temperature and time applications. Temperature indicating devices are prepared by applying single sided strips of Tesa 4965 8.0 mil thickness adhesive strips. Upon heating above or near the irreversible ink below its normal temperature transition point, the rapid onset of color development occurs.

Time indicating strips are prepared by applying single sided strips of Tesa 4965 8.0 mil thickness. Adhered adhesive color developer/color former constructs are left at room temperature for 14 days. Color development is monitored over time and compared to a stationary reference color and correlated with time during the color development process.

B Low Temperature Time-Temperature Indicating Devices Using Pre-Mixed Color Forming Compositions and Activating Adhesives:

Pre-mixed color forming compositions and inks are utilized as time and time temperature indicating systems in combination with activating adhesives above. Labels are die-cut in-line. Reference color graphics are simultaneously printed in-line using color hues and intensities calibrated as reference colors for given temperature and time applications. Temperature indicating devices are prepared by laminating, but separated with removable pull tab single sided strips of Tesa 4965 8.0 mil thickness.

Upon applying a time-temperature indicating device to a cold food product and allowing for quick cooling of the indicating device, the device is activated by removing the pull tab. Color development remains dormant at refrigerator temperatures (40-45° F.) for several days. Upon removing the adhered activated device from refrigerator temperatures to room temperature, color development begins occurring within the first 1-3 hours of elevated temperature exposure (72° F.). Color development continues with continued elevated exposure and at each time duration matched a predetermined reference color calibrated to a given exposure time.

C. Obscured Graphic Time and Time Temperature Sensors Using Pre-Mixed Color Forming Compositions and Activating Adhesives:

Pre-mixed color forming compositions and inks are utilized as time and time temperature indicating systems in combination with activating adhesives as above. Visible obscuring graphics are generated in combination with pattern printed sensitive ink patterns.

Labels are die-cut in-line. Reference color graphics are simultaneously printed in-line using color hues and intensities calibrated as reference colors for given temperature and time applications. Temperature indicating devices are prepared by applying single sided strips of Tesa 4965 8.0 mil thickness adhesive strips. Upon heating above or near the irreversible ink below its normal temperature transition point, the rapid onset of color development occurs.

Time indicating strips are prepared by applying single sided strips of Tesa 4965 8.0 mil thickness. Adhered adhesive color developer/color former constructs are left at room temperature for 14 days. Color development is monitored over time and compared to a stationary reference color and correlated with time during the color development process. Graphics and colorations are designed and printed to optimize the appearance of an image through the overlay patterns. The resulting image development process improves the end-point appearance of a temperature and/or time delay pattern.

D. Time and Time Temperature Sensors Using Long Chain Alcohols and Activating Adhesives:

Long chain alcohols can be used to regulate, mitigate, slow, and modulate color development in a time and temperature dependent way. Specifically, and especially utilizing an adhesive activating means in conjunction, long chain alcohols have the advantage of acting as a passive carrier for color formers, but have a highly mitigating effect on causing color development. Their transition melting temperatures can accommodate a wide range of time and time temperature applications.

A mixture containing 0.5 gm Magenta 20 (Hilton Davis, LLC) and 2.5 gm Unilin 700 series (Baker Hughes Inc.) is heated above the co-mixed melting transitions (greater than 100° C.) until both components are completely solubilized. The transparent solution is thoroughly mixed and directly coated on substrates from the melt. Further melting is accomplished after coats are applied to improve uniformity and adsorption into substrates.

Temperature indicating devices are prepared by applying single sided strips of Tesa 4965 8.0 mil thickness adhesive strips. Upon heating above or near the melting transition of the Unilin 700 series alcohol, the rapid onset of magenta color development occurrs.

Time indicating strips are prepared by applying single sided strips of Tesa 4965 8.0 mil thickness. Adhered adhesive color developer/color former constructs are left at room temperature for 14 days. Color development is monitored over time and compared to a stationary reference color and correlated with time during the color development process.

E. Reversible/Irreversible Ascending Temperature Monitoring:

Magenta 20 is mixed at 10% by weight with glycerol monostearate (GMS), heated, and dissolved. The heating process leads to a color development in the melt as GMS acts both as a solvent to the color former as well as a color developer. The molten mixture is printed on paper and film substrates. Upon cooling the intense color reverses to a clear transparent state as the GMS solidifies. Color development is reversible with hot and cold temperature cycling above and below the melting transition of GMS.

Temperature indicating devices are prepared by applying single sided strips of Tesa 4965 8.0 mil thickness. Upon heating above or near the melting transition of GMS, the rapid onset of magenta color development occurrs. Color development becomes irreversible in the presence of adhesive coated regions. In contrast, color development is reversible in areas on non-adhesive coated regions.

Multi ascending reversible and irreversible temperature indicating and irreversible time indicating devices may be prepared for monitoring various medium to high temperature process and control steps. Printed areas become an ascending reversible thermochromic layer as well as an irreversible heat sensitive time temperature ink in the presence of an adhesive activating layer for a plurality of optical sensing capabilities.

F. High Temperature—Time Indicating Constructs:

Pre-mixed color forming compositions and inks are utilized as time and time temperature indicating systems in combination with activating adhesives. 60° C., 75° C., 90° C. and 100° C. irreversible thermochromic ink compositions (Kromagen and/or Kromax concentrate, Thermographic Measurement Co.) are flexographically printed using a 20 anilox roller on various paper and film stocks (pressure sensitive and non-pressure sensitive stock types). Magenta, orange, cyan, blue, turquoise, green, black and red color types are printed.

Labels are die-cut in-line. Reference color graphics are simultaneously printed in-line using color hues and intensities calibrated as reference colors for given temperature and time applications. Temperature indicating devices are prepared by applying single sided strips of Tesa 4965 8.0 mil thickness alone or in combination with a blocking layer adhesive (Arlon 301 transfer adhesive 2.0 mil thickness). Upon heating above or near the irreversible ink below its normal temperature transition point, the rapid onset of color development occurrs with out the blocking or delay layer (160° F. for 10-60 minutes). Delayed color development occurs using the block or delay layer (160° F., 1-3 hours).

G. Hydrocarbon Blocking and Delay Layers:

Blocking and delay layers are produced with micro-crystalline waxes, paraffins, and pure hydrocabon layers and coatings. Pre-mixed color forming compositions and inks are utilized as time and time temperature indicating systems in combination with activating adhesives printed as above. Hydrocarbon compositions are post coated in fractional mil thicknesses directly onto the pre-mixed color forming compositions and inks.

Labels are die-cut in-line. Reference color graphics are simultaneously printed in-line using color hues and intensities calibrated as reference colors for given temperature and time applications. Temperature indicating devices are prepare by applying single sided strips of Tesa 4965 8.0 mil thickness alone or in combination with a blocking layer adhesive (Arlon 301 transfer adhesive 2.0 mil thickness). Upon heating above or near the irreversible ink below its normal temperature transition point, the rapid onset of color development occurs with out the blocking or delay layer (160° F. for 10-60 minutes). Delayed color development occurs using the block or delay layer (160° F., 1-3 hours).

H. Color Referenced Time Security Badge an 24 Your Promotional Label Using Pre-Mixed Color Forming Compositions and Activating Adhesives:

Pre-mixed color forming compositions and inks are utilized as time and time temperature indicating systems in combination with activating adhesives. 60° C., 75° C., 90° C. and 100° C. irreversible thermochromic ink compositions (Kromagen and/or Kromax concentrate, Thermographic Measurement Co.) are flexographically printed using a 20 anilox roller on various paper and film stocks (pressure sensitive and non-pressure sensitive stock types). Magenta, orange, cyan, blue, turquoise, green, black and red color types are printed.

Labels are die-cut in-line. Reference color graphics are simultaneously printed in-line using color hues and intensities calibrated as reference colors for given temperature and time applications. Time indicating security badges and promotional labels are prepared as by applying single sided strips of Tesa 4965 8.0 mil thickness. Adhered adhesive color developer/color former constructs are left at room temperature for 0-24 hours. Color development is monitored over time and compared to a stationary reference color and correlated with time during the color development process.

I. Time Indicating Graphic Comprising a Thermally Printed Security Label:

Pre-mixed color forming compositions and inks are utilized as time and time temperature indicating systems in combination with activating adhesives. 60° C., 75° C., 90° C. and 100° C. irreversible thermochromic ink compositions (Kromagen and/or Kromax concentrate, Thermographic Measurement Co.) are flexographically printed using a 20 anilox roller on various paper and film stocks (pressure sensitive and non-pressure sensitive stock types). Magenta, orange, cyan, blue, turquoise, green, black and red color types are printed on pressure direct thermal label stock as an adjunct security badge.

The security badge can be directly thermally printed with visitor, date, time, and intended information using a digital thermal printer, print driver, and operating software. Printed graphics are designed such that the direct thermal print information is printed in regions other than where the time-dependent color former ink composition is printed.

Labels are die-cut in-line. Reference color graphics are simultaneously printed in-line using color hues and intensities calibrated as reference colors for given temperature and time applications. Temperature indicating devices are prepare by applying single sided strips of Tesa 4965 8.0 mil thickness. Upon heating above or near the irreversible ink below its normal temperature transition point, the rapid onset of color development occurs.

Time indicating strips are prepared by applying single sided strips of Tesa 4965 8.0 mil thickness to regions where the color forming ink is printed adjacent to where direct thermal print mater is printed using the thermal printer. Adhered adhesive color developer/color former constructs are monitored periodically for time-based security applications at room temperature from 1-48 hours. Color development is monitored over time and compared to a stationary reference color and correlated with time during the color development process.

J. Direct Thermal Paper Conversion to Time Indicating Devices:

Commercially available direct thermal coated substrates are converted into a time only indicating substrate depending upon the thermal coating composition and provided protective coating. An aggressive adhesive overlay containing a solvent and acidic polymeric adhesive is applied at room temperature to the direct thermal label. The thermal label is sourced from thermal label supplier and printed with various overlay graphics. The thermal label type is minimally coated with a protective layer so that the onset of color development in the direct thermal coating can be activated with the adhesive overlay.

Color development is monitored at room temperature and daily over time to observe color development. After 1 day a light gray begins to appear. Daily, the color begins to gradually develop until the gray begins to become more saturated. The gray color development process is compared to a gray scale. The gray scale is calibrated graphically so that the color development process can be matched and compared against an ascending daily schedule. Various short and long time frame duration indicators are developed for a variety of time scales and product timing applications.

K. Direct Thermal Paper Conversion to Short Duration Time-Temperature Indicating Label:

Commercially available direct thermal coated substrates are converted into a time only indicating substrate depending upon the thermal coating composition and provided protective coating. An aggressive adhesive overlay containing a solvent and acidic polymeric adhesive is applied at room temperature to the direct thermal label. The thermal label is sourced from thermal label supplier and printed with various overlay graphics. The thermal label type is minimally coated with a protective layer so that the onset of color development in the direct thermal coating may be activated with the adhesive overlay in combination with moderately high temperatures.

Color development is monitored at 160° F. over time to observe color development. After 15 minutes the color begins to become lightly gray. Hourly, the color begins to deepen until the gray begins to become more saturated. The gray color development process is compared to a gray scale. The gray scale is calibrated graphically so that the color development process can be matched and compared against an ascending hourly schedule. Various short and long time frame duration indicators are developed for a variety of time scales and product timing applications. Different time and temperature profiles are developed depending on the commercially available thermal label stock and the aggressive nature of the color developing adhesive layer comprising the activating laminate.

L. Aqueous PAA Solution Co-Mixed with Microcrystalline Color Former:

Polyacrylic acids including molecular weight cutoffs from 800 grams/mol to 10,000,000 grams/mole are formulated as color developing carrier resins with micro-particulate color forming agents. Aqueous suspensions or dispersions are made with individual molecular weight type of PAA's. PAA's are dissolved or suspended at between 1-10% by weight in water. Solution pH may be adjusted accordingly to increase or decrease acidity.

Milled or ground suspension of micro-crystalline color formers Magenta 20, green, orange, red, yellow or (Hilton Davis, LLC), crystal violet (Sigma Aldrich Co.), or orange, magenta, red, black, blue, or green (Ciba Corp), are admixed with the aqueous solutions of each PAA. After complete mixing or emulsification, the ink-like solutions can be printed directly on to paper or film substrates. Profiles for temperature and time temperature readings are recorded.

M. Promotional Time-Color Development Using Metallochromic Effect:

Pre-mixed color forming compositions and inks are utilized as time and time temperature indicating systems in combination with activating adhesives. 60° C., 75° C., 90° C. and 100° C. irreversible thermochromic ink compositions (Kromagen and/or Kromax concentrate, Thermographic Measurement Co.) are further formulated with high luster aluminum powders/pastes to provide a metallic luster. Aluminum powders/pastes are added at between 2-15% by weight depending on the metallic luster desired. Samples are printed using a 20 anilox hand roller on various paper and film stocks (pressure sensitive and non-pressure sensitive stock types). Magenta, orange, cyan, blue, turquoise, green, black and red color types are formulated and printed.

Labels are die-cut in-line. Reference color graphics are simultaneously printed in-line using color hues and intensities calibrated as reference colors for given temperature and time applications. Temperature indicating devices are prepared by applying single sided strips of Tesa 4965 8.0 mil thickness. Upon heating above or near the irreversible ink below its normal temperature transition point, the rapid onset of color development occurs Time indicating strips prepared are by applying single sided strips of Tesa 4965 8.0 mil thickness. Adhered adhesive color developer/color former constructs are left at room temperature for up to 7 days. Initial printed samples give a rich silver metallic luster. Color development is monitored over time and compared to a stationary reference color and correlated with time during the color development process. Final colors are brilliant mixtures of metallic luster and color former types selected.

N. Full Color Image Development:

Three color graphics are produced of images at 200 DPI and color separation is performed. Color separated flexographic plates are produced using standard processes. Pre-mixed color forming ink bases including red, blue, and green are printed in a three color flexographic printing process in the undeveloped state using a Mark Andy flexographic printing press.

Images are die-cut in-line. Temperature indicating images are prepared by applying single sided strips of Tesa 4965 8.0 mil thickness. Upon heating above or near the irreversible ink below its normal temperature transition point, the rapid onset of color development occurs. Time indicating images are prepared by applying single sided strips of Tesa 4965 8.0 mil thickness. Adhered adhesive color developer/color former constructs are left at room temperature for up to 7 days.

N. Holographic Overlays for Special Optical Effects:

Holographic and optical overlays are utilized in conjunction with image and pattern development using time and time temperature compositions. Translucent holographic overlay graphics and Fresnel lenses and prisms are superimposed with printed patterns of the color forming layer. The optical overlay can be adhered to one side or a double-stick adhesive color development layer such that the laminated structure is transparent and yet can be aligned with a printed color forming layer for the laminate to be adhered to. The superposition of optical overlays and the printed color forming printed graphic provide for unique and specialized optical effects. For example, time and time temperature dependent images can be developed to provide motion or 3-D effects during the color development process.

O. Time-Temperature Indicating Thermometer:

An ascending irreversible color indicating thermometer is made using time and time temperature compositions. The thermometer is designed to initiate a color development process at temperature exposures to or above 165° F. for greater than 5 seconds. The thermometer comprises an activating adhesive layer, a thermal blocking layer, and a commercially available direct thermal label stock. The layered construct is assembled, die-cut, and adhered to a flat plastic pointed probe 0.25 inch wide and 4 inches in length. The plastic probe is pointed on one end for easy insertion into heated products such as foods, meats, poultry, and the like.

P. Color Disappearing Time Indication Composition and Construct:

Pre-mixed color forming compositions and inks are utilized as time and time temperature indicating systems in combination with activating adhesives. 60° C., 75° C., 90° C. and 100° C. irreversible thermochromic ink compositions (Kromagen and/or Kromax concentrate, Thermographic Measurement Co.) are flexographically printed using a 6 anilox roller on various paper and film stocks (Mark Andy printing press, pressure sensitive and non-pressure sensitive stock types).

Magenta, orange, cyan, blue, turquoise, green, black and red color types are printed. Labels are die-cut in-line. Beginning reference color graphics are simultaneously printed in-line using color hues and intensities calibrated as reference colors for given temperature and time applications.

Color forming/developing inks are exposed to elevated temperature to develop the respective colors, patterns and images. Bright vivid colors develop above the threshold temperature of the irreversible inks. Colors are maintained and stable at room temperature for prolonged storage periods.

Color decaying adhesive layers are prepared using pH base adjusted water-based adhesives. Adhesives are coated on a clear plastic film backing and protected with a release layer to make pressure sensitive color decaying adhesive strips. The color decaying adhesive strips are die-cut and prepared as pressure sensitive labels in roll stock form.

Time indicating strips are prepared by applying single sided adhesive to the pre-color developed/printed substrates. Adhered adhesive color decaying constructs are left at room temperature for 24 hours. Color development is monitored over time and compared to a stationary reference color and correlated with time during the color development process. As time progresses, the color decays relative to the pre-printed reference colors.

The extent to which color decay may be accelerated depends on the pre-coloration conditions of the pre-colored printed mediums, the chemical diffusiveness of the substrate printed on, the final pH adjusted basic conditions of the color decaying adhesive composition, mobilizing tackifying compositions used in the adhesive layer, time and temperature and the like.

Q. Low Time Temperature Color Decaying Indicating Composition and Construct:

Pre-mixed color forming compositions and inks are utilized as time and time temperature indicating systems in combination with color decaying adhesives above. Labels are die-cut in-line. Reference color graphics are simultaneously printed in-line using color hues and intensities calibrated as reference colors for given temperature and time applications. Temperature indicating devices are prepared by laminating, but are separated with removable pull tab single sided strips of the adhesive layer prepared as described above.

Upon applying a time-temperature indicating device to a cold food product and allowing for quick cooling of the indicating device, the device is activated for color decay by removing the pull tab. Color decay remains dormant at refrigerator temperatures (40-45° F.) for several days. Upon removing the adhered activated device from refrigerator temperatures to room temperature, color decay begins occurring within the first 1-3 hours of elevated temperature exposure (72° F.). Color development continues with continued elevated exposure and at each time duration matched a pre-determined reference color calibrated to a given exposure time.

R. Color Dissipating Marking Means for Time Indication:

Pre-mixed color forming compositions and inks are utilized as time and time temperature indicating systems in combination with activating adhesives. 60° C., 75° C., 90° C. and 100° C. irreversible thermochromic ink compositions (Kromagen and/or Kromax concentrate, Thermographic Measurement Co.) are flexographically printed using a 6 anilox roller on various paper and film stocks (Mark Andy printing press, pressure sensitive and non-pressure sensitive stock types).

Magenta, orange, cyan, blue, turquoise, green, black and red color types are printed. Labels are die-cut in-line. Beginning reference color graphics are simultaneously printed in-line using color hues and intensities calibrated as reference colors for given temperature and time applications.

Color forming/developing inks are exposed to elevated temperature to develop the respective colors, patterns and images. Bright vivid colors develop above the threshold temperature of the irreversible inks. Colors are maintained and stable at room temperature for prolonged storage periods.

Color decaying marking inks are prepared using pH base adjusted water-based resins. Felt tip ink marking pens are filled to make color decaying marking pens. The color decaying pens are cap sealed and prepared for use with color developed printed mediums. Ancillary fluorescent colors additives may be used as tracer compositions and to provide additional optical features to the color developing marks.

Time indicating strips are prepared by using the pre-color developed/printed substrates. Time indicating color decaying strips are marked and left at room temperature for marked color dissipation. Color decay is monitored over time and compared to a stationary reference color and correlated with time during the color development process. As time progresses, the color decays relative to the pre-printed reference colors.

The extent to which color decay may be accelerated or decelerated depends on the pre-coloration conditions of the pre-colored printed mediums, the chemical diffusiveness of the substrate printed on, the final pH adjusted basic conditions of the color decaying ink composition, and the like.

S. Plural Messaging Message Development/Message Decay Time Indication Composition and Construct for Price Tag Evolution:

Pre-mixed color forming compositions and inks are utilized as time and time temperature indicating systems in combination with activating adhesives. 60° C., 75° C., 90° C. and 100° C. irreversible thermochromic ink compositions (Kromagen and/or Kromax concentrate, Thermographic Measurement Co.) are flexographically printed using a 6 anilox roller on various paper and film stocks (Mark Andy printing press, pressure sensitive and non-pressure sensitive stock types).

Magenta, orange, cyan, blue, turquoise, green, black and red color types are printed, but printed messages, pricing information and colors are not developed. Labels are die-cut in-line. These printed areas are registered as areas where information would appear over time using the adhesive development layer. Beginning reference color graphics are simultaneously printed in-line using color hues and intensities calibrated as reference colors for given temperature and time applications.

In a second location of the printed labels, printed messages, pricing information and colors are developed using heat as developer. These locations are sequestered relative to the undeveloped regions and registered as areas where information disappears or decays over time using an adhesive layer formulated to dissipate the printed-activated areas.

Labels are die-cut in-line. Color forming/developing inks are exposed to elevated temperature to develop the respective colors, patterns and images. Bright vivid colors develop above the threshold temperature of the irreversible inks. Colors are maintained and stable at room temperature for prolonged storage periods.

Color decaying adhesive layers are prepared using pH base adjusted water-based adhesives. Adhesives are coated on a clear plastic film backing and protected with a release layer to make pressure sensitive color decaying adhesive strips. The color decaying adhesive strips are die-cut and prepared as pressure sensitive labels in roll stock form.

Color activating adhesive layers are prepared as spot printed adhesives describe above. Both activating and decaying adhesives are coated on a clear plastic film backing and protected with a release layer to make pressure sensitive color decaying adhesive strips. Position of each activating and decaying adhesive types are registered according the corresponding regions of developed or undeveloped inks representing the respective pricing information, patterns and images.

Corresponding price and message changing labels are prepared by applying adhesives to the pre-color developed/printed substrates and non-developed regions. Adhered adhesives demonstrate shifts in the decaying portion of the construct over a 30 day period so that original messaging and pricing disappears over time. Likewise, the color generating/developing adhesive layer demonstrates shifts in the message area showing new pricing information appearing over the same 30 day period.

Pricing and messaging formats for the appearance of new information and disappearance of original information find use in a number of pricing, promotional, advertising, inventory control, security and other commercial, retail, industrial, service, and other fields where users need only apply one label or article and that label or article would shift in information over a desired timeframe.

The extent to which color decay can be accelerated or decayed depends on the pre-coloration conditions of the pre-colored printed mediums, the chemical diffusiveness of the substrate printed on, the final pH adjusted basic conditions of the color decaying adhesive composition, mobilizing tackifying compositions used in the adhesive layer, time and temperature and the like.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A color change composition comprising a color former and color developer that transitions from a first color state to a second color state upon application of an applied stimulus, wherein the color developer comprises a glycerol monostearate derivative.

2. The color change composition according to claim 1, wherein the applied stimulus is a temperature stimulus.

3. The color change composition according to claim 1, wherein the applied stimulus is solvation.

4. The color change composition according to claim 1, wherein the applied stimulus is hydration.

5. The color-change composition according to claim 1, wherein the applied stimulus is provided by an RFID device.

6. The color change composition according to claim 1, wherein the transition is reversible.

7. The color change composition according to claim 1, wherein the transition is irreversible.

8. The color change composition according to claim 1, wherein the transition is uniform.

9. The color change composition according to claim 1, wherein the transition exhibits hysteresis.

10. The color change composition according to claim 1, wherein the color former is a thermochromic dye.

11. The color-change composition according to claim 1, wherein the color-change composition comprises an adhesive.

12. The color change composition according to claim 1, wherein the composition comprises two or more distinct leuco dyes.

13. The color change composition according to claim 12, wherein the two or more distinct leuco dyes exhibit opposing color transition characteristics in response to the same applied stimulus.

14. The color change composition according to claim 1, wherein the one or more of the components of the color change composition is micro-encapsulated.

15. The color change composition according to claim 1, wherein the color change composition changes color in a time dependent manner.

16. The color change composition according to claim 1, wherein the color change composition changes color in a time and temperature dependent manner.

17. A substrate comprising a color change composition according to claim 1 present on a least one surface thereof.

18. The substrate according to claim 17, wherein the color change composition is present on the at least one surface in the form of a pre-determined pattern.

19. The substrate according to claim 18, wherein the pre-determined pattern has a machine readable format.

20. A method comprising applying a quantity of a color change composition according to claim 1 to a surface of a substrate.

21. The color change composition according to claim 1, wherein the color developer comprises a polydiacetylene.

* * * * *